(12) United States Patent
Yamakawa et al.

(10) Patent No.: US 9,062,392 B2
(45) Date of Patent: Jun. 23, 2015

(54) METHODS FOR ISOLATING A PEPTIDE METHODS FOR IDENTIFYING A PEPTIDE

(75) Inventors: Mineo Yamakawa, Campbell, CA (US); Joseph V. Kosmoski, Los Altos, CA (US); Deane C. Little, Los Altos, CA (US)

(73) Assignee: INTEL CORPORATION, Santa Clara, CA (US)

( * ) Notice: Subject to any disclaimer, the term of this patent is extended or adjusted under 35 U.S.C. 154(b) by 1170 days.

(21) Appl. No.: 12/267,099

(22) Filed: Nov. 7, 2008
(Under 37 CFR 1.47)

(65) Prior Publication Data
US 2015/0133305 A1    May 14, 2015

Related U.S. Application Data

(63) Continuation-in-part of application No. 10/749,532, filed on Dec. 30, 2003, now abandoned.

(51) Int. Cl.
*C40B 30/04* (2006.01)

(52) U.S. Cl.
CPC ................................. *C40B 30/04* (2013.01)

(58) Field of Classification Search
None
See application file for complete search history.

(56) References Cited

U.S. PATENT DOCUMENTS

| | | | |
|---|---|---|---|
| 4,737,578 A | 4/1988 | Evans et al. | |
| 5,401,511 A | 3/1995 | Margalit | |
| 5,603,872 A | 2/1997 | Margalit | |
| 5,679,548 A * | 10/1997 | Barbas et al. | 435/69.6 |
| 5,874,409 A * | 2/1999 | Victoria et al. | 514/15 |
| 6,180,341 B1 * | 1/2001 | Iverson et al. | 435/6 |
| 6,514,767 B1 | 2/2003 | Natan | |
| 6,656,712 B1 | 12/2003 | Balavoine et al. | |
| 2002/0068272 A1 * | 6/2002 | Larocca et al. | 435/5 |
| 2003/0113714 A1 | 6/2003 | Belcher et al. | |
| 2008/0182760 A1 * | 7/2008 | Hayashizaki | 506/42 |
| 2010/0184606 A1 * | 7/2010 | Janssen et al. | 506/2 |

FOREIGN PATENT DOCUMENTS

WO    WO 0179479    * 10/2001

OTHER PUBLICATIONS

Carninci, P. et al, Methods in Enzymology, vol. 303, pp. 19-44 (1999).*
Freeman et al, Science, 267, 1995, 1629-1632.
Puntes et al, Science, 291, Mar. 2001, 2115-17.
Lee et al, Science, 296, May 2002, 892-95.
Naik et al, Nature, 2002, 169-172.
Letherbrow et al. (1991). "Structure of Immunoglobulin G by Scanning Tunneling Microscopy" *J. Mol. Biol.* 221:361-365.
Dorn et al. (1999). "High-resolution AFM-Imaging an Mechanistic Analysis of the 20 A Prteasome", *J. Mol. Biol* 288:1027-1036.
Doering et al., "Spectroscopic Tags Using Dye-Embedded Nanoparticles and Surface-Enhanced Raman Scattering", Analytical Chemistry, :5-9.
Lee et al, "Ordering of Quantum Dots Using Genetically Engineered Viruses" Sci. 296:892-895 (May 2002).
Mulvaney et al., "Glass-Coated, Analyte-Tagged Nanoparticles: A New Tagging System Based on *Detection* with Surface-Enhanced Raman Scattering", Am Chem Soc. 19-4784-4790 (2003).
Ulman, Abraham, "Formation and Structure of Self-Assembled 7 Monolayers," Chem. Rev., 96:1533-1544.
Chapman et al., "Properties of Inhibin Binding to Betaglycan, InhBP/p120 and the Activin Type II Receptors," Molecular and Cellular Endocrinology, 2002, 196:19-93.

* cited by examiner

*Primary Examiner* — Christian Boesen
(74) *Attorney, Agent, or Firm* — Pillsbury Winthrop Shaw Pittman LLP

(57) ABSTRACT

The present invention is directed to methods, for example phage display assays, for bioengineering peptides that bind to individual distinct nucleotides. Also provided are peptides engineered by such methods. Specifically, cyclic peptides that bind individual distinct nucleotides are provided herein.

6 Claims, 4 Drawing Sheets

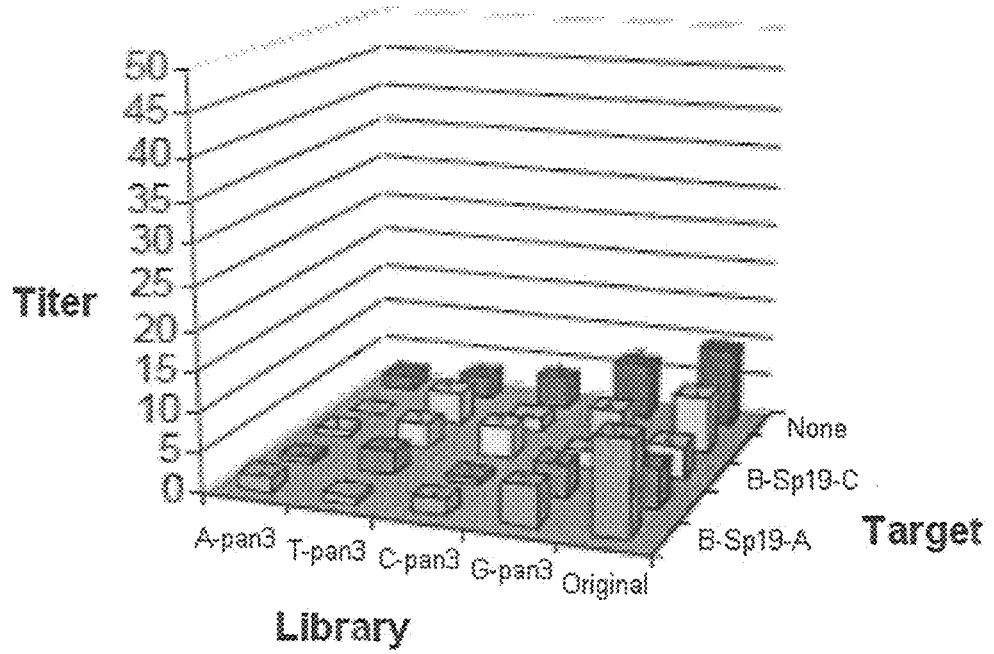

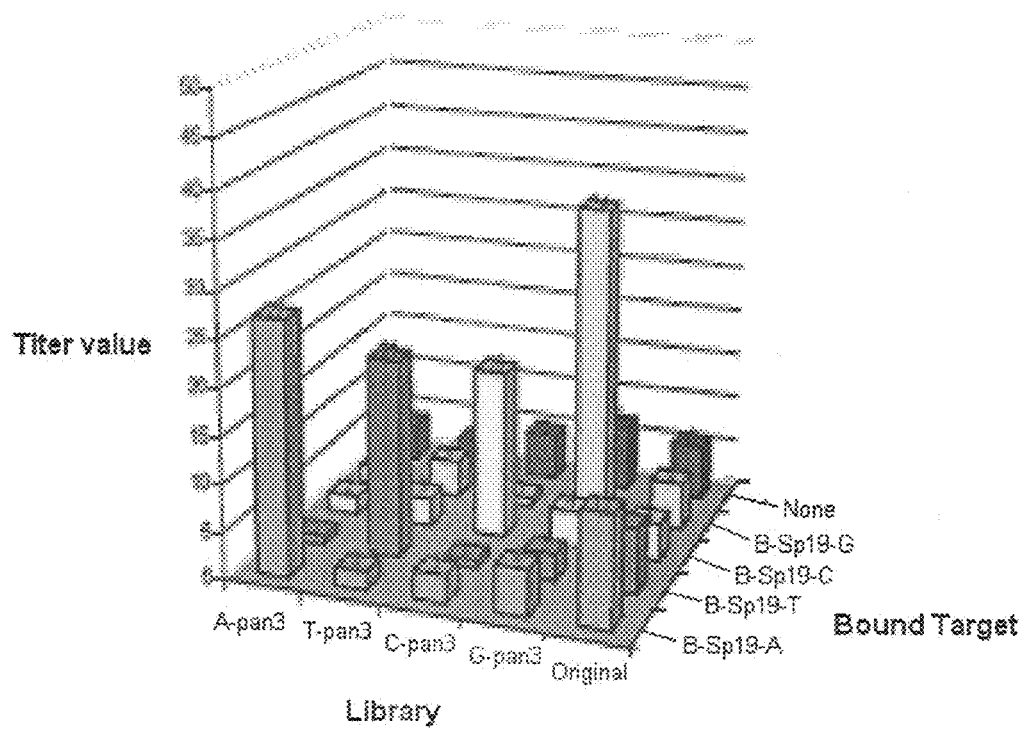

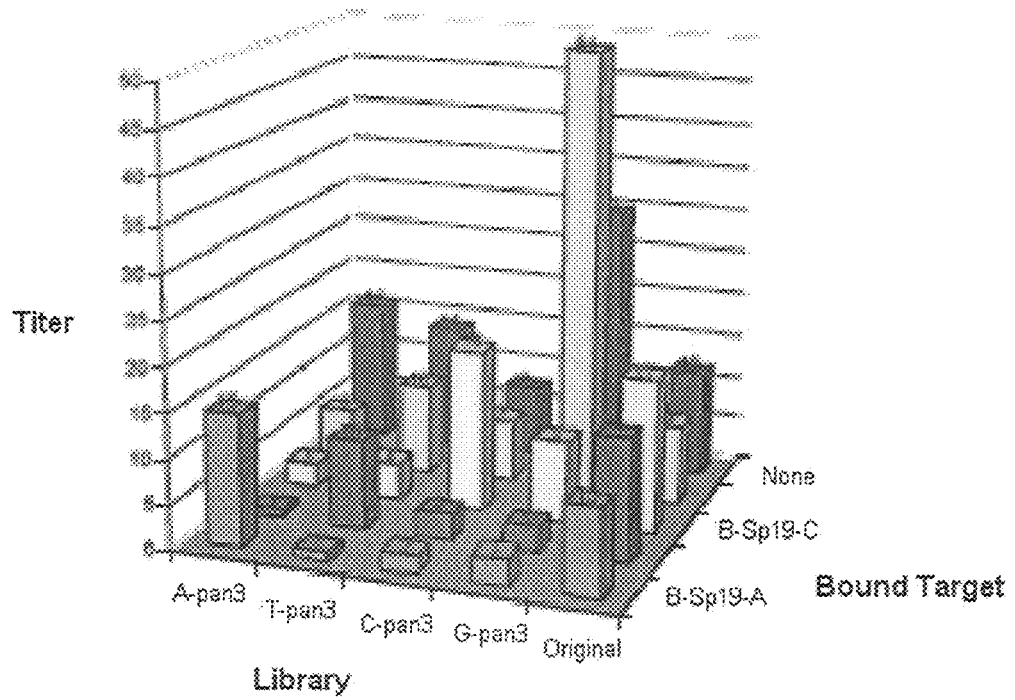

METHODS FOR ISOLATING A PEPTIDE METHODS FOR IDENTIFYING A PEPTIDE

RELATED APPLICATION

This application is a continuation-in-part of application Ser. No. 10/749,532, filed Dec. 30, 2003, which is incorporated herein in its entirety by reference.

FIELD OF THE INVENTION

The invention relates generally to selective recognition, and more specifically to selective recognition of geometrical shapes and individual nucleotides with unique peptides.

BACKGROUND

Advances in medicine such as new diagnostic techniques require highly sophisticated bioreactors, microelectronics, microelectrodes, and biomolecular analysis techniques, for example for use in sensitive biosensors. Powerful analytical techniques such as scanning probe microscopy (SPM) have been developed, along with powerful tagging techniques in which very small structures called nanotags, are used to identify larger molecules such as biomolecules. The detection of nanotags and biomolecules using these powerful analytical techniques requires binding of the nanotags and biomolecules to substrates that are anatomically flat and sometimes highly hydrophobic, which are difficult surfaces for nanotag and biomolecular binding. Thus, a need exists for methods and compositions that can be used to facilitate binding of nanotags and biomolecules to anatomically flat and hydrophobic substrates.

In general, attachment and binding of biomolecules such as peptides and polypeptides to specific materials and substrates involve, for example, chemical adsorption and hydrophobic/hydrophilic interactions, or chemical reactions such as binding of a thiol group of a peptide to gold. However, often peptide or polypeptide binding to a very hydrophobic and atomically flat surface is very difficult often resulting in denaturization or conformational changes of the peptide structure. Presently no good solutions for reliable binding of peptides or polypeptides to such surfaces are known. For example highly ordered/oriented pyrolytic graphite (HOPG) is a popular and common substrate used for holding deposits of samples for SPM scanning. However, peptides and polypeptides tend to be non-uniformly deposited after being dried without any specific protocols. Thus, a need exists for peptides that specifically bind to atomically flat surfaces, and for methods to identify these peptides.

BRIEF DESCRIPTION OF THE FIGURES

The present invention will be better understood by reference to the Detailed Description of the Invention when taken together with the attached figures, wherein:

FIG. 2 shows phage titer results from a positive control experiment (wash solution was titered).

FIG. 3 shows phage titer results after bumping bound phage with a distinct nucleotide.

FIG. 4 shows phage titer results after bumping bound phage with the non-specific disruption buffer DTT.

DETAILED DESCRIPTION OF THE INVENTION

Definitions

Figure 1:
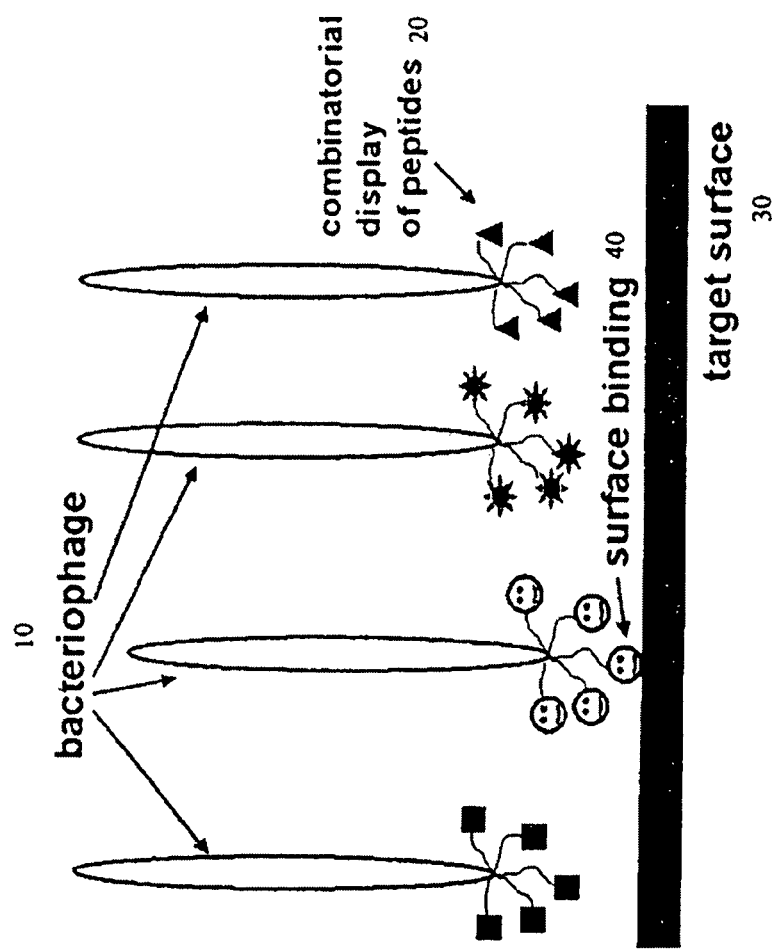
FIG. 1 diagrammatically illustrates a combinatorial display of peptides, wherein a specific peptide binds a flat surface.

Peptides or polypeptides that bind to a flat surface or a smooth, curved surface are referred to herein as "surface-binding peptides or polypeptides" or "binder peptides or polypeptides."

Biomolecules as used herein include, but are not limited to, nucleic acids, peptides, proteins, polysaccharides, and combinations thereof, as well as other biological substrates, inhibitors, activators, ligands, hormones, or cytokines.

"Nucleic acid" encompasses DNA, RNA (ribonucleic acid), single-stranded, double-stranded or triple stranded and any chemical modifications thereof. Virtually any modification of the nucleic acid is contemplated. A "nucleic acid" can be of almost any length, from oligonucleotides of 2 or more bases up to a full-length chromosomal DNA molecule. Nucleic acids include, but are not limited to, oligonucleotides and polynucleotides. A "polynucleotide," as used herein, is a nucleic acid molecule that includes at least 25 nucleotides. An "oligonucleotide," as used herein, is a nucleic acid molecule that includes at least 2 nucleotides.

As used herein, the term "specific binding pair member" refers to a molecule that specifically binds or selectively hybridizes to another member of a specific binding pair. Specific binding pair member include, for example, an oligonucleotide and a nucleic acid to which the oligonucleotide selectively hybridizes, or a protein and an antibody that binds to the protein. A "target" or "analyte" molecule includes, but is not limited to, a nucleic acid, a protein, a lipid, and a polysaccharide.

A "nucleotide" is composed of a nitrogenous base, a five carbon sugar, and at least one phosphate group. In the present invention, a "nucleotide" can be one of the five nucleotides used for DNA and RNA synthesis, i.e., A, T, C, G, U. In other embodiments, the nucleotide is an analog of the five aforementioned nucleotides. For the purposes of this invention, a "nucleotide" refers to the common nucleotides and analogs thereof. In addition, salts of nucleotides and nucleotide analogs are included within the definition of "nucleotide."

Nucleotide analogs (and salts thereof) are well known in the art. For example, U.S. Pat. No. 5,886,179 describes nucleotide phosphonate esters, and is hereby incorporated by reference in its entirety.

Non-limiting examples of nucleotide analogs include Adenosine 2':3'-cyclic monophosphate, Adenosine 3',5'-cyclic monophosphate, Adenosine 5'-monophosphoramidate, Adenosine 5'-O-thiomonophosphate, Adenylosuccinic acid, 8-Azidoadenosine 3':5'-cyclic monophosphate, 8-Azido-cyclic adenosine diphosphate-ribose, 8-Bromoadenosine 5'-monophosphate, 5-Bromo-2'-deoxyuridine, 8-Bromoguanosine 5'-monophosphate, $N^2$-Butyrylguanosine 3':5'-cyclic monophosphate, Cytidine 2':3'-cyclic monophosophate, 5-Bromouridine 5'-triphosphate, Cytosine β-D-arabinofuranoside 5'-monophosphate, 2'-Deoxyadenosine 3':5'-cyclic monophosphate, 2'-Deoxyadenosine 3'-monophosphate, 2'-Deoxyadenosine 5'-triphosphate, 2'-Deoxycytidine 3'-monophosphate, 2'-Deoxycytidine 5'-monophosphate, 2'-Deoxyguanosine 5'-diphosphate, 2'-Deoxyguanosine 3'-monophosphate, 2'-Deoxyguanosine 5'-monophosphate, 2'-Deoxyguanylyl(3'→5-2'-deoxyguanosine, 2'-Deoxyinosine 5'-triphosphate, $P^1,P^6$-Di(adenosine-5') hexaphosphate, $P^1,P^4$-Di(adenosine-5)tetraphosphate, $P^1,P^4$-Di(adenosine-5)tetraphosphate, $P^1,P^3$-Di(adenosine-5') triphosphate, $N^6,2'$-O-Dibutyryladenosine 3',5'-cyclic monophosphate, $N^6,2'$-O-Dibutyryladenosine 3',5'-cyclic monophosphate, $N^2$,2'-O-Dibutyrylguanosine 3',5'-cyclic monophosphate, 2',3'-Dideoxyguanosine 5'-triphosphate, $P^1$,$P^4$-Di(guanosine-5')tetraphosphate, $P^1$,$P^4$-Di(guanosine-5')tetraphosphate, DMT-Thymidine H-phosphonate, $N^6$-Ethenoadenosine 3':5'-cyclic monophosphate, 1,$N^6$-Ethenoadenosine 5'-monophosphate, 1,$N^6$-Etheno-2'-deoxyadenosine 5'-monophosphate, 5-Fluoro-2'-deoxyuridine 5'-monophosphate, Guanosine 5'-diphosphate, Guanosine 5'-triphosphate, Guanosine 5'-monophosphomorpholidate 4-morpholine-N,N'-dicyclohexylcarboxamidine salt, Guanosine 5'-[β-thio]diphosphate trilithium salt, Guanosine 5'-[γ-thio]triphosphate tetralithium salt, 8-Hydroxyadenosine 3':5'-cyclic monophosphate, Inosine 3':5'-cyclic monophosphate sodium salt, 5-Iodouridine 5'-monophosphate sodium salt, 5-Iodouridine 5'-triphosphate sodium salt, 5-Mercuricytidine carbonate 5'-triphosphate triethylammonium salt, $N^6$-Methyladenosine 5'-monophosphate sodium salt, α,β-Methyleneadenosine 5'-diphosphate sodium salt, α,β-Methyleneguanosine 5'-diphosphate sodium salt, β,γ-Methyleneguanosine 5'-triphosphate sodium salt, 7-Methylguanosine 5'-diphosphate sodium salt, 7-Methylguanosine 5'-triphosphate sodium salt, 2-Methylthioadenosine 5'-monophosphate triethylammonium salt hydrate, $N^6$-Monobutyryladenosine 3':5'-cyclic monophosphate sodium salt, $N^6$-Monobutyryl-2'-deoxyadenosine 3':5'-cyclic monophosphate sodium salt, 2'-O-Monobutyrylguanosine 3':5'-cyclic monophosphate, 2'-O-Monosuccinyladenosine 3':5'-cyclic monophosphate tyrosyl methyl ester, 3-Pyridinealdehyde adenine dinucleotide, Thymidine 3':5'-cyclic monophosphate, Thymidine-5'-diphosphoglucose disodium salt, Thymidine-5'-diphospho-α-D-glucose disodium salt, Uridine 3':5'-cyclic monophosphate, Uridine 5'-diphosphogalactose disodium salt and Uridine 2'-monophosphate.

A "single distinct nucleotide," or "individual distinct nucleotide," refers to a nucleotide of a unique molecular structure. The methods of the present invention evolve peptides that are selective for a "single distinct nucleotide" over other nucleotides that may be in a solution mixture. A "single distinct nucleotide" can be a "nucleotide analog," and is preselected by the user of the method. Therefore, the methods of the present invention evolve peptides that are selective for a "pre-selected nucleotide.

A peptide that is selective for a "single distinct nucleotide" or a "pre-selected nucleotide" over other nucleotides, exhibits at least 10 fold specificity for the "single distinct nucleotide" or "pre-selected nucleotide" over the other nucleotides that are present in a mixture.

A "cyclic peptide" is a peptide whose amino and carboxyl termini are linked with a peptide bond. In the present invention, the cyclic peptides include from about 5 amino acids to about 50 amino acids.

"Biopanning" refers to the process of contacting a peptide library with a ligand population, followed by separation of the peptides that bind the ligand population from the peptides that do not bind the ligand population. Next, one of these subpopulations (i.e., bound-peptides or unbound peptides) is amplified. If multiple rounds of biopanning take place, the amplified subpopulation is used in the next contacting step.

"Panning" refers to the contacting and separation step of the biopanning process.

A "bump" reaction (or "bumping") is a reaction that disrupts (i.e., "disruption reaction") or potentially disrupts a phage's binding to its respective target.

A "heterogeneous population" refers to a population of molecules that includes at least two or more variants. In the present invention, heterogeneous population is used to refer to a population of nucleotides or oligonucleotides that includes nucleotides other than a pre-selected nucleotide. For example, if the pre-selected nucleotide is "A," a heterogeneous population of nucleotides may include T, C, G, U and any non-natural (synthetic) nucleotides. Similarly, a heterogeneous population of oligonucleotides can include oligonucleotides comprised of T, C, G, U and any non-natural (synthetic) nucleotides (if the pre-selected nucleotide is "A").

A "homogeneous population" refers to a population of molecules that includes only one variant. In the present invention, homogeneous population is used to refer to a population of nucleotides or oligonucleotides that consist essentially of a pre-selected nucleotide. For example, if the pre-selected nucleotide is "A," the homogeneous population of nucleotides will include "A," but not other nucleotides. Similarly, a homogeneous population of homo-oligonucleotides (oligomers) will include homo-oligomers of "A" (adenine).

In one aspect, the present invention is directed to a method for isolating a peptide. The method entails contacting a first peptide library comprising a first subset of peptides with a first set of nucleotides comprising a heterogeneous population of nucleotides other than a pre-selected nucleotide, to identify a first sub-library of peptides comprising a second subset of peptides that do not bind to the first set of nucleotides. Next, the first sub-library of peptides is contacted with a homogeneous population of the pre-selected nucleotide, to identify a second sub-library of peptides that bind to the pre-selected nucleotide. Finally, the method entails isolating at least one peptide from the second sub-library of peptides.

In a further aspect of the invention, the first peptide library is a sub-library preselected from an initial peptide library, by at least two rounds of biopanning.

In yet a further aspect of the invention, the at least two rounds of biopanning comprise two contacting steps with two different ligand populations, wherein the first ligand population comprises a homogeneous population of homo-oligonucleotides that comprise nucleotides other than the pre-selected nucleotide, and the second ligand population comprises a homogeneous population of homo-oligonucleotides that comprise the pre-selected nucleotide.

In still a further aspect of the invention, an initial round of biopanning is carried out prior to the at least two rounds of biopanning. The initial round comprises contacting the initial peptide library with a heterogeneous population of single stranded oligonucleotides to identify an initial sub-library of peptides that bind single stranded nucleic acid oligonucleotides.

In still another aspect of the invention, peptides that selectively bind pre-selected nucleotides, or single distinct nucleotides, are provided.

In a further aspect, the peptides that selectively bind pre-selected nucleotides are cyclic peptides.

Methods for bioengineering (e.g., discovering/identifying, designing, and/or synthesizing) molecules that can bind to geometrically and/or atomically structured (e.g., flat, fractal or random) molecular surfaces of a structure/substrate, are provided herein. This type of binding is required in a variety of analytical preparations including SPM (e.g., AFM and STM) scanning of samples such as nanocodes, which can be, for example, peptide based molecules such as enzymes, glycoproteins, oligopeptides, or synthetic nanotags. Also, immobilizing peptide-based biomolecules such as antibodies (i.e., glycoproteins) and reaction enzymes (e.g., kinases and phosphorylases) for biosensors, bioreactors, microelectronics, and microelectrode requires this type of binding.

Phage display technology allows the rapid discovery, identification, and selection of target peptides with appropriate chemical and/or physical characteristics, compared to a selection by theoretical or intuitive guesswork, which takes a significant amount of time and effort, if successful at all. Thus, methods provided herein utilize phage display to discover new materials for use in analytical preparations and devices, and new circuit structures for processing and decoding information. Furthermore, compositions and methods provided herein include molecular combinations of two or more defined activities to provide a family of building blocks to create nano-molecular scaffoldings and attachment sites. These nano-molecular scaffolding and attachment sites allow reading, decoding, and computations based on (bio)molecules and allow creation of new electronic circuits, for example.

Accordingly, methods to bio-engineer peptide-based molecules that possess specific chemical and/or physical affinities for geometrically or atomically specific structured/patterned surfaces, is provided. The peptides are useful, for example, for attaching nanocodes to a substrate surface for enabling reliable and accurate barcode reading (i.e., encoding and decoding information in nanotags).

Accordingly, in one embodiment a method is provided for identifying a peptide that binds to a surface having a target geometrical shape or a target atomic configuration, that includes contacting the surface having the target geometrical shape with a library of peptides or polypeptides, and identifying the peptides or polypeptides that bind to the surface having the target geometrical shape or atomic configuration. In certain aspects, each peptide or polypeptide is associated with an encoding polynucleotide. These aspects facilitate isolation and sequencing of the encoding polynucleotide.

In another embodiment, a method is provided for identifying a peptide that binds to a surface having a target geometrical shape, that include contacting the surface having the target geometrical shape with a phage display library under reaction conditions, wherein the phage express a peptide, and identifying peptides that bind to the surface having the target geometrical shape.

In certain aspects, the library of peptides or polypeptides is generated using straight chemical synthesis instead of using a phage display library (See e.g. on the world wide web at dkfz-heidelberg.de/cbpl/; and Houghten et al., Nature, 354: 84 (1991)). For example, a chip-based peptide library can be screened for peptides that bind a surface having a target geometrical shape. Alternatively, bacteria can be used for creating combinatorial peptides, as is known in the art. The library, for example, can include more than 1,000, 10,000, 100,000, 1,000,000, or 10,000,000 unique peptides. In one specific, non-limiting example, the library includes 34 million hexa-peptides.

In another aspect, a polypeptide that binds to a surface having a target geometrical shape is identified by immunizing a mammalian organism, such as, for example a rodent or a human, with a surface having the target geometrical shape, and identifying antibodies against the target geometrical shape that are produced by the organism. Methods for immunizing mammalian organisms and identifying antibodies are known in the art. Also, fragments of the antibody, such as Fab fragments, can be isolated. Furthermore, antigen binding regions of identified antibodies that bind the target geometrical shape can be isolated.

A geometrical shape is a characteristic surface configuration. An atomic configuration is the arrangement of atoms of a surface, and optionally the surrounding solvation sphere. In certain aspects, the target geometrical shape of the surface is a flat surface, or a very flat surface. In other aspects, the target geometrical shape of the surface is a smooth surface, such as a smooth, curved surface. For example, the smooth, curved surface can be that of a nanotube. In other examples, the anatomic configuration is periodic, fractal, or random. Furthermore, the surface, in certain examples, is hydrophobic.

A flat surface is an even surface that is free from roughness, irregularities, or projections. A flat surface can be non-curved or curved. A smooth surface is a surface that is free from roughness, irregularities, or projections. A smooth, curved surface is a surface that deviates from straightness in a continuous way that is free from roughness, irregularities, or projections. A structure with a periodic atomic configuration is a structure that is composed of a specific molecular configuration that occurs at repeated intervals. A surface with a fractal atomic configuration is a surface that is composed of, an unusual number of dimensions (e.g., 2.381 dimensions) and that looks essentially the same, regardless of the magnification. A surface with a random atomic configuration is a surface that is composed of molecules that have no specific pattern or organization.

As is known, any surface with properties/structures similar to, for example, annealed gold, HOPG, and/or Teflon® are considered to be atomically very flat by SPM microscopy. A silicon surface is considered to be "flat" by SPM microscopy. Fractal dimensions are an index of complexity and/or "flatness" or "smoothness" depending on the scales if fractal dimension is constant.

A surface that is bound by surface-binding peptides and polypeptides disclosed herein, can be, for example, a flat surface or another smooth surface, such as a smooth, curved surface. Furthermore, the surface can include organic and/or inorganic components. For example, the surface can be a substrate for an analytical or measurement device such as a substrate for scanning probe microscopy (SPM), or any other analytical or measurement device that can utilize a flat surface or a smooth, curved surface. An SPM substrate can be a graphite substrate, for example, such as a highly ordered pyrolytic graphite (HOPG) substrate. In another aspect, the surface is a carbide or graphite electrode, which can be used for example, in nanotube production. In other examples, the surface-binding peptides identified herein bind semiconductor surfaces.

The surface can be composed of a wide-variety of components. For example, the surface can be composed, at least in part, of boron nitride, lead sulfide, zinc selenide, cadmium selenide, cadmium sulfide, gallium arsenide, aluminum arsenide, zinc sulfide, gallium nitrate, indium phosphate, or gallium arsenide. In other aspects, the surface includes mica, silicon, or annealed gold. In other examples, the surface is composed, at least in part, of Teflon®.

Phage display library generation and screening in general are known in the art (See e.g., Barbas, C., et al., "Phage Display A Laboratory Manual," Cold Spring Harbor (2001); and Kay et al., Methods 24, 240-246 (2001)). Phage display libraries can be constructed using known methods, or they can be purchased (e.g., from New England BioLabs (Beverly, Mass.)). As shown in FIG. 1, the methods provided herein involve a binding assay that includes contacting a library of phage 10 (e.g., M13 filamentous phage), each displaying a different exogenous peptide sequence 20 on the surface of the bacteriophage 10, to a target surface 30, such as a graphite surface, with a specific geometrical pattern or geometrical shape such as an atomically flat structure 30. After exposure of the phage 10 to the target surface 30 for an appropriate incubation period to allow binding, unbound phage 10 are washed away and the specifically bound phage 10 are eluted or specifically removed.

Eluted phage are amplified, and the process is repeated, for example for a total of 2-20 rounds, more specifically, for example for 2-10 rounds, and even more specifically, for example for 3-4 rounds. The screening of phage display libraries for surface-binding peptides through multiple rounds of screening, as disclosed herein, is referred to as biopanning. Phage are amplified using known methods, for example by reinfecting host bacteria with the phage and culturing the reinfected host bacteria. In certain embodiments, DNA of identified phage is amplified by using an in vitro amplification procedure such as the polymerase chain reaction PCR.

The incubation period for binding of the phage to the surface can be any typical incubation period for a phage display assay, such as, for example, about 5 minutes to about 1 day, or more specifically from 15 minutes to 4 hours. In a specific example the incubation occurs for 2 hours. Elution or removal of specifically bound phage typically involves use of harsh conditions to inhibit the interaction of the peptide to the substrate. For example, an elution solution of an extreme pH (e.g., 1-3, 8-12), or which includes a denaturing agent such as urea, and/or a protease, such as trypsin, can be used.

Phage display engineering has been used to discover peptides that bind to nanoparticles/quantum dots (S. Lee, et al., Science 2002, 296:892). Numerous groups have reported that "plate binders" are in vast excess to other desired activities, yet these plate binders have been overlooked as desirable lead compounds. (Barbas, C., et al., "Phage Display A Laboratory Manual," Cold Spring Harbor, 2001). Furthermore, as illustrated in the examples herein, peptides have been identified using phage display methods that bind to plastics surfaces.

In certain aspects, each round of evolution (or biopanning) of methods disclosed herein, is designed to fit the parameters of "the common denominator principle". In brief, the principle states that desired elements are present in every evolution step, although presented differently, sometimes by eliminating undesired elements.

Accordingly, in certain aspects, methods disclosed herein utilize combinatorial directed evolution. According to combinatorial directed evolution methods, peptides are identified using several rounds of biopanning. In certain aspects, at least 2, 3, 4, 5, 6, 7, 8, 9, 10, 15, 20, and 25 rounds of biopanning are performed by repeating the contacting, identifying, and amplifying steps. During each successive round of biopanning, for example, the reaction conditions can be made more stringent than the prior round. More stringent conditions are conditions in which a higher affinity (i.e., a lower dissociation constant) of the peptide for the surface is required for the peptide to bind to the surface. Parameters such as pH, ionic strength, concentration of metal ion, and temperature changes, for example, can affect binding of a peptide to a surface. More stringent conditions can be provided, for example, by acidifying or alkylating an incubation buffer for the binding reaction or by increasing the temperature of the incubation.

If a specific peptide sequence that has negative affinities to other specific geometrical structures of a material surface is required, the binding assay can include both positive and negative selection pressure. Positive selection is generally used to select for affinity whereas negative selection often enhances specificity. Peptide sequences with non-specific binding can also be eliminated.

As an example of an aspect that uses negative selection to remove unwanted peptides, peptides identified in one or more rounds of screening of a surface with a target geometrical shape or atomic configuration, are placed in contact with a surface with an identical or substantially identical chemical composition but an undesirable geometrical shape and/or atomic configuration. Substantially identical chemical compositions include the same major chemical constituents but can include minor differences in chemical constituents. Phage that do not bind the surface with the undesirable geometrical shape and/or atomic configuration, are collected and optionally amplified and subjected to additional rounds of biopanning. For example, the surface with the undesirable geometrical shape or atomic configuration, can be composed of crystals and therefore have a surface that is not flat. Phage that bind to the crystals can be eliminated. The rounds of selection and removal can be repeated to increase the binding strength and/or specificity of identified phage. Combinations of desirable/undesirable characteristics for screening phage libraries include, for example, screening for peptides that bind a flat geometry or a smooth, curved geometry, but do not bind a crystal, or screening for peptides that bind a periodic atomic configuration but not a random atomic configuration.

In certain aspects, in addition to the desired geometrical shape and/or atomic configuration, the target surface can have additional desired properties. For example, the surface can have certain chemical properties in addition to a desired geometrical shape and/or atomic configuration. In these aspects, for example, phage can be identified that bind to a flat surface or a smooth, curved surface but only if it is hydrophobic, negatively charged, or positively charged.

As a specific example, phage can be screened for binding to flat, hydrophobic surfaces in general. Historically, it has been difficult to identify peptides that bind to a surface with these characteristics. Accordingly, in this specific aspect, different flat, hydrophobic surfaces can be used to identify a peptide that binds many different flat and hydrophobic surfaces. A peptide with these characteristics is valuable for example, to assist in coating of biomolecules and/or nanocodes to SPM substrates.

In certain aspects, the phage is amplified using a sloppy amplification reaction during one or more rounds of biopanning. A "sloppy amplification reaction" is a reaction utilizing a process known as sloppy PCR, error-prone PCR or mutagenic PCR (PCR Primer, A Laboratory Manual, Cold Spring Harbor Laboratory Press (1995)). Error-prone, sloppy, or mutagenic PCR is a process for performing the polymerase chain reaction under conditions where the copying fidelity of the DNA polymerase is low, such that a high rate of point mutations is obtained along the entire length of the PCR product. This process increases the diversity of peptides in the phage library after initial round(s) of biopanning identify at least weakly binding peptides.

Accordingly, methods of the present invention involve the use of phage display technology to identify, through combinatorial directed evolution, specific amino acid sequence(s) of a peptide that preferentially bind to a specific material surface of a geometrically distinct structure, such as a substrate for a measurement devices or analytical instrument that utilize substrates of particular shapes or atomic configuration, such as scanning probe microscopy (SPM). In certain aspects of the invention, the surface to which the surface-binding peptides or polypeptides of the present invention bind, is composed, at least in part, of an elemental carbon-containing molecule. The term "elemental carbon-containing molecule" generally refers to allotropic forms of carbon. Examples include, but are not limited to, diamond, graphite, activated carbon, $carbon_{60}$, carbon black, industrial carbon, charcoal, coke, and steel. Other examples include, but are not limited to carbon planchet, highly ordered pyrolytic graphite (HOPG), single-walled nanotube (SWNT), single-walled nanotube paste, multi-walled nanotube, multi-walled nanotube paste as well as metal impregnated carbon-containing materials.

The surface to which the surface-binding peptides and polypeptides disclosed herein bind can be a substrate or a surface of a substrate. A "substrate" can be a microfabricated solid surface to which molecules attach through either covalent or non-covalent bonds and includes, e.g., silicon, Langmuir-Bodgett films, functionalized glass, germanium, ceramic, silicon, a semiconductor material, PTFE, carbon, polycarbonate, mica, mylar, plastic, quartz, polystyrene, gallium arsenide, gold, silver, metal, metal alloy, fabric, and combinations thereof capable of having functional groups such as amino, carboxyl, thiol or hydroxyl incorporated on its surface. Similarly, the substrate may be an organic material such as a protein, mammalian cell, antibody, organ, or tissue with a surface to which a biologic material may attach. The surface may be large or small and not necessarily uniform but should act as a contacting surface (not necessarily in monolayer). The substrate includes a contacting surface that may be the substrate itself or a second layer (e.g., substrate or biologic material with a contacting surface) made of organic or inorganic molecules and to which organic or inorganic molecules may contact. Regardless of its specific composition, a surface according to the present invention is a target geometrical shape or atomic configuration, as disclosed herein.

Previous development of self-assembly monolayers utilize a bi-phasic kinetic model in which a surfactant is absorbed to a surface due to both affinity for the surface and already bound surfactants (Ulman, A., "Formation and Structure of Self-Assembly Monolayers," Chem. Rev. 1996, 96:1533-1554). The methods disclosed herein provide the advantage that the interdependence of the two binding events, one to the surface and the other to already bound surfactants, can be controlled though selective pressure for either. Accordingly, in certain aspects, the surface used for a method for identifying a peptide disclosed herein is composed at least in part, or is bound by, a surfactant. An identified phage expressing a surface-binding peptide can bind to the surfactant or to both the surface and the surfactant. Alternatively, the surfactant, for example, can be a monolayer that covers the surface such that peptides expressed on the phage bind to the surfactant but cannot bind to the surface.

As discussed above, methods disclosed herein include selection and identification of high affinity binding sequences through appropriate assays of the peptide, also referred to as peptide ligands, with affinities to specific geometrical structures of a material surface by biopanning (i.e., an in vitro selection process). In certain methods disclosed herein, a physical linkage exists between peptide from a large library of random peptide sequences and a nucleic acid encoding each sequence. Therefore, after biopanning, individual clones are isolated and sequenced using methods well known in the art. According to these methods, a particular DNA sequence encoding a peptide that demonstrates specific binding to a specific geometrical shape or atomic configuration-binding is identified.

The resulting selected DNA sequences are used to identify corresponding amino acid sequences of a surface-binding peptide. The identified peptide using methods disclosed herein, can be separately synthesized (e.g., by peptide synthesizer) and its positive and/or negative binding affinities and binding specificity can be confirmed by appropriate assays as will be understood.

Accordingly, in another embodiment an isolated peptide or polypeptide is provided that binds a flat surface, a smooth surface (e.g., a smooth, curved surface) or a surface with a desired atomic configuration. The identified peptide can include natural or non-natural amino acids (i.e. unnatural amino acids), or combinations thereof. Numerous non-natural amino acids and methods for incorporating such non-natural amino acids into peptide chains are known in the art and can be used with the methods herein (See e.g., Hohsaka et al., Nucleic Acids Research, 29, 17 3646-3651 (2001)). Non-natural amino acids can include almost any group as the R group. In certain aspects, the non-natural amino acid is an isotopic analog, such as C13. C13 amino acids can be used, for example, for NMR experiments. In certain aspects, non-natural amino acids are incorporated into a peptide by using specifically-designed and charged tRNAs that recognize stop codons. In more specific non-limiting examples, the peptide can include Nitrophenylalanine (nitroPhe), -Nitrobenzoxadiazolyl-L-lysine residues, or the selenium-containing tryptophan "analog" b-selenolo[3,2-b]pyrrolylalanine, or any other non-natural amino acid known in the art. Furthermore, in another embodiment, an isolated phage is provided, that includes the surface-binding peptide or polypeptide.

In certain aspects, the surface-binding peptides and/or polypeptides are bound to nanoparticles such as carbon nanotubes. The surface-binding peptides and/or polypeptides bound to nanotubes can be used, for example, to bind an array of the nanotubes to a substrate. The nanotube arrays bound to a substrate can be used in a variety of applications, including, but no limited to, fabrication of miniature electronic, chemical and molecular devices, probes for use in scanning probe microscopy, molecular wires, incorporation into ultrafast random access memory (Rueckes et al., Science 289:94, 2000), field-effect transistors, single electron transistors, field emitter arrays, flat screen panels, electromechanical transducers, molecular switches, and any other known use for carbon nanotube arrays.

The methods and compositions disclosed herein can be used to provide a "mix and match" combinatorial application of desired activities to create a "toolbox" or kit of assembly units. Thus, after identifying a particular surface-binding peptide sequence by phage display, the identified peptide can be replicated into multiple linked units of the same (or similar) or different identified surface-binding peptide sequences. Recombinant DNA technologies can be used to construct coding sequences that encode these peptides, or the peptides can be directly synthesized, as will be understood. For example, if a certain peptide sequence, A-B-C-D-E (where A-E denote amino acids) is discovered to be a good surface binder, a variety of linked permutations of the peptide, such as (A-B-C-D-E)-(A-B-C-D-E)-(A-B-C-D-E)-(A-B-C-D-E), can be used. Various linkers can be used to attach such peptides to create "extended" surface binder peptides. Many linkers are known in the art and can be used. Therefore, the identified surface-binding peptides disclosed herein can be used as stand-alone specific surface-binding peptide sequences as well as "structures" containing multiple (e.g., two or more, three or more, four or more, five or more) chemically linked sequences that can include the same or similar sequence.

Accordingly, in another embodiment, an isolated peptide or polypeptide that includes at least two peptide units, is provided, wherein each peptide unit specifically binds a target geometrical shape or atomic configuration. In certain aspects, the isolated peptide or polypeptide is a recombinant peptide or polypeptide in that it includes about 2, 3, 4, 5, 6, 7, 8, 9, 10, 11, 12, 13, 14, 15, 20, 25, 50, 100 peptide units that are not included in a tandem configuration in a known, natural protein. In certain examples, at least 2 of the peptide units include a different amino acid sequence. As used herein, "about" means within ten percent of a value. For example, "about 100" would mean a value between 90 and 110. The isolated peptide or polypeptide provided herein is typically identified using the method for identifying a peptide disclosed above, and individual surface-binding peptides can include, for example, between about 2 and 100 amino acids, between about 5 and 50, and more specifically, for example, between about 7 and 20 amino acids.

In another aspect, the isolated peptide or polypeptide can be associated with a nanocode. In fact, surface-binding peptides or polypeptides can become a supportive part of an encoded nanocode, or other type of nanotag. In another aspect, the peptide units are linked by a linkage other than a peptide bond, for which many are known in the art, including, for example, Isocynate, phosphoramidite, carboxide, glycol, and azide. As disclosed above, the peptide can be associated with a nanocode.

Surface-binding peptides identified using methods disclosed herein, can be used for a variety of applications. As indicated above, the surface-binding peptides can be used in substrates for scanning probe microscopy (SPM), in biosensors, in electrodes and in semiconductors, for example. Accordingly, in another embodiment, a scanning probe microscopy (SPM) substrate is provided that has a flat surface or a smooth, curved surface, to which a surface-binding peptide or polypeptide is bound. In certain aspects, surface-binding peptides are bound to the substrate in an ordered arrangement.

Any of the many known SPM substrates can be used with the present invention, as long as the substrate has a flat surface or a smooth, curved surface, or a surface with a periodic, fractal, or random atomic configuration. Therefore, the surface, for example, can be composed of glass, ceramic, plastic, polystyrene, polypropylene, polyethylene, polycarbonate, PTFE (polytetrafluoroethylene), PVP (polyvinylpyrrolidone), germanium, silicon, quartz, gallium arsenide, gold, silver, nylon, nitrocellulose or any other material known in the art that is capable of acting as an SPM substrate and having a flat surface or a smooth, curved surface, or a surface with a periodic, fractal, or random atomic configuration. In certain embodiments of the invention the surface is a glass slide or cover slip. In another specific non-limiting example, the surface is a carbon lattice in a fullerene building block structure such as corannulene.

In certain aspects, the SPM substrate is a graphite substrate. In another aspect, the surface-binding peptide or polypeptide bound to the SPM substrate is associated with a biomolecule such as a polypeptide, a polynucleotide, a carbohydrate, or a combination thereof. For example, the surface-binding peptide or polypeptide bound to the SPM substrate can be associated with an enzyme or an antibody. The surface-binding peptide or polypeptide is typically identified using the methods disclosed herein before being bound to the SPM substrate. Furthermore, as disclosed herein, the peptide can include between about 2 and 100, about 5 to 50, and more specifically between about 7 and 20 amino acids, for example.

In another aspect, a biomolecule that is associated with a surface-binding peptide that is bound to an SPM substrate, is bound to a nanoparticle also referred to as a nanotag, such as a nanocode. A "nanocode" is a composition that can be used to detect and/or identify a probe physically associated with the nanocode. In non-limiting examples, a nanocode includes one or more submicrometer metallic barcodes, carbon nanotubes, fullerenes or any other nanoscale moiety that can be detected and identified by scanning probe microscopy. Nanocodes are not limited to single moieties, and in certain embodiments of the invention a nanocode can include, for example, two or more fullerenes attached to each other.

Where the moieties are fullerenes, they can, for example, have a series of large and small fullerenes attached together in a specific order. The order of differently sized fullerenes in a nanocode can be detected by scanning probe microscopy and used, for example, to identify an attached probe. Nanocodes can be used in many different methods, for example methods such as, but not limited to, polynucleotide sequencing, immunoassays, single nucleotide polymorphism (SNP) detection, specific genotype detection, and ligand binding, as well as personal ID and security protocols.

Accordingly, in another embodiment a method is provided, wherein a surface-binding peptide or polypeptide is contacted with an SPM substrate having a flat surface, wherein the surface-binding peptide binds to the flat surface. Furthermore, the bound surface-binding peptide or polypeptide can be functionalized and contacted with a nanoparticle or a biomolecule or a combination thereof, wherein the nanoparticle or biomolecule or combination thereof, bind to the surface-binding peptide or polypeptide. A population of surface-binding peptides or polypeptides can be aligned on the SPM substrate to align biomolecules that bind to the surface-binding peptides or polypeptides.

Methods for functionalizing peptides are known in the art. For example a bifunctional linker can be added using a bifunctional cross-linking reagents (e.g., available from Sigma-Aldrich, St. Louis, Mo.). The bifunctional cross-linking reagents can be divided according to the specificity of their functional groups, e.g., amino, guanidino, indole, or carboxyl specific groups. Of these, reagents directed to free amino groups are popular because of their commercial availability, ease of synthesis and the mild reaction conditions under which they can be applied. Exemplary methods for cross-linking molecules are disclosed in U.S. Pat. Nos. 5,603,872 and 5,401,511. Cross-linking reagents include glutaraldehyde (GAD), bifunctional oxirane (OXR), ethylene glycol diglycidyl ether (EGDE), and carbodiimides, such as 1-ethyl-3-(3-dimethylaminopropyl) carbodiimide (EDC).

If necessary, an appropriate immobilization and dispersion technique can be used to improve the SPM analysis. For example, in SPM methods a substrate surface treatment such as thiol-gold, polylysine, silanization/AP-mica, as well as Mg.sup.2+ and/or Ni.sup.2+ (See e.g., Proc. Natl. Acad. Sci. USA 94:496-501 (1997); Biochemistry 36:461 (1997); Analytical Sci. 17:583 (2001); Biophysical Journal 77:568 (1999); and Chem. Rev. 96:1533 (1996)) can be used to uniformly disperse and immobilize a surface-binding peptide or polypeptide before binding a biomolecule to the peptide or polypeptide. Furthermore, peptide sequences can be identified using methods disclosed herein, that give rise to single or multiple dimension matrices along the surface. Not to be limited by theory, these structures are more likely to form considering biphasic surface chemistry kinetics observed with thiolated probes on gold surfaces.

Scanning probe microscopy (SPM) is well known in the art. Examples of SPM include scanning tunneling microscopy (STM), atomic force microscopy (AFM), lateral force microscopy (LFM), and chemical force microscopy (CFM). Other SPM modes that could benefit from the surface-binding peptides and polypeptides disclosed herein include magnetic force microscopy (MFM), high frequency MFM, magnetoresistive sensitivity mapping (MSM), electric force microscopy (EFM), scanning capacitance microscopy (SCM), scanning spreading resistance microscopy (SSRM), tunneling AFM and conductive AFM.

In another embodiment, a biosensor is provided that includes a substrate having a flat surface, or a smooth, curved surface, wherein a surface-binding peptide or polypeptide is bound to the flat surface or smooth, curved surface of the biosensor. In one aspect, the surface-binding peptide or polypeptide is associated with a biomolecule such as a polypeptide, a polynucleotide, a carbohydrate, or a combination thereof. For example, the peptide or polypeptide can be associated with an enzyme or an antibody. The surface-binding peptide or polypeptide is typically identified using the methods disclosed herein before it is associated with the biosensor. Furthermore, as disclosed herein, the peptide can include between about 2 and 100, about 5 and 50, or more specifically, for example between about 7 and 20 amino acids.

Accordingly, in another embodiment a method is provided, wherein a surface-binding peptide or polypeptide is contacted with a biosensor surface having a flat surface wherein the surface-binding peptide binds to the flat surface. Furthermore, the bound surface-binding peptide or polypeptide can be functionalized and contacted with a specific binding pair member, wherein the specific binding pair member binds to the surface-binding peptide or polypeptide. For example, surfaces with a bound surface-binding peptide or polypeptide that is contacted with a specific binding pair member, can be used to form a substrate for an ELISA assay or can be formed based on a modified ELISA assay.

In general, biosensors have two components: a highly specific recognition element and a transducing structure that converts the molecular recognition event into a quantifiable signal. Signal transductions are generally accomplished with electrochemical, field-effect transistor, optical absorption, fluorescence or interferometric devices. Biosensors have been developed to detect a variety of biomolecular complexes including oligonucleotide pairs, antibody-antigen, hormone-receptor, enzyme-substrate and lectin-glycoprotein interactions. Flat or smooth, curved surfaces of biosensors, or surfaces of other target geometries, can be coated with surface-binding peptides or polypeptides in order to facilitate attachment of biomolecular specific binding pair members. The surface-binding peptides and polypeptides can be bound to surfaces of either the recognition element or the transducing element.

In another embodiment, A biochip is provided that includes a substrate having a flat surface, or smooth, curved surface, wherein a surface-binding peptide or polypeptide is bound to the flat surface or smooth, curved surface of the biochip. In one aspect, the surface-binding peptide or polypeptide is associated with a biomolecule such as a polypeptide, a polynucleotide, a carbohydrate, or a combination thereof. For example, the peptide or polypeptide can be associated with an enzyme or an antibody. The surface-binding peptide or polypeptide is typically identified using the methods disclosed herein before it is associated with the biosensor. Furthermore, as disclosed herein, the surface-binding peptide or polypeptide can include between about 2 and 100, about 5 and 50, or more specifically, for example between about 7 and 20 amino acids.

Accordingly, in another embodiment a method is provided, wherein a surface-binding peptide or polypeptide is contacted with a biochip surface having a flat surface, or smooth, curved surface, wherein the surface-binding peptide binds to the flat surface, or smooth, curved surface. Furthermore, the bound surface-binding peptide or polypeptide can be functionalized and contacted with a specific binding pair member, wherein the specific binding pair member binds to the surface-binding peptide or polypeptide. As such, the methods provide for a biochip with a surface-binding probe attached to the biochip surface and optionally also bound to a specific binding pair member. The biochips can be used, for example, to identify an analyte that binds the specific binding pair member.

Non-limiting examples of substrates that can be used with biochip embodiments include glass, silica, silicate, PDMS (poly dimethyl siloxane), silver or other metal coated substrates, nitrocellulose, nylon, activated quartz, activated glass, polyvinylidene difluoride (PVDF), polystyrene, polyacrylamide, other polymers such as poly(vinyl chloride) or poly(methyl methacrylate). Non-limiting examples of assays that can be performed on biochips that include the surface-binding peptides of the present invention include footprinting assays using Fenton chemistry, which is amenable to solid phase activity, and ELISA assays. For each of these examples, catalytic activities can be associated with the biochip through the surface-binding peptides.

In another embodiment, a graphite or carbide electrode is provided, that has a flat surface or a smooth, curved surface, wherein a surface-binding peptide or polypeptide is bound to the flat surface or the smooth, curved surface of the graphite or carbide electrode. Graphite and carbide electrodes are well known in the art as being useful, for example, in the synthesis of carbon nanotubes, such as by Krtschmer are methods (W. Krtschmer, W. et al., Nature 347, 354-358 (1990)). Graphite naturally has a flat surface as one of the crystal surface axes unless it is burned/scorched or modified by high voltages. The graphite electrode surface is very difficult to functionalize using traditional methods. The graphite or carbide electrodes with bound peptides of the present invention are useful, for example, for attaching catalysts, such as metallic particles, to the surface of the electrodes and can be used in biosensors and fuel cells.

Accordingly, in another embodiment a method is provided, wherein a surface-binding peptide or polypeptide is contacted with a graphite or carbide electrode having a flat surface or a smooth, curved surface, wherein the surface-binding peptide binds to the flat surface or the smooth, curved surface. Furthermore, the bound surface-binding peptide or polypeptide can be functionalized and contacted with catalyst metallic particles.

In another embodiment, a semiconductor is provided that includes a substrate composed of a semiconductor material, and a surface-binding peptide or polypeptide that is bound to a surface of the substrate, wherein the surface has a flat, or a smooth, curved geometry. The peptide or polypeptide is a surface-binding peptide or polypeptide disclosed herein. The semiconductor substrate, for example includes a Group II-VI semiconductor material. For example, the semiconductor material can include silicon, boron nitride, lead sulfide, zinc selenide, cadmium selenide, cadmium sulfide, gallium arsenide, aluminum arsenide, zinc sulfide, gallium nitrate, indium phosphate, or gallium arsenide. The semiconductor can form all or a portion of a biosensor. Surface binder peptides identified using methods disclosed herein, can be used as a connecting/binding linkers between organic materials and semiconductor (surfaces).

Semiconductor nanocrystals exhibit size and shape-dependent optical and electrical properties. These diverse properties result in their potential applications in a variety of devices such as light emitting diodes (LED), single electron transistors, photovoltaics, optical and magnetic memories, and diagnostic markers and sensors. Control of particle size, shape and phase is also critical in protective coatings such as car paint and in pigments such as house paints. The semiconductor materials can be engineered to be of certain shapes and sizes, wherein the optical and electrical properties of these semiconductor materials can best be exploited for use in numerous devices. The surface-binding peptides and polypeptides disclosed herein provide a means for binding substances to a semiconductor nanocrystal when the nanocrystal has a flat surface or a smooth, curved surface, or when the surface of the nanocrystal has a periodic, fractal, or random atomic configuration.

In another embodiment, a kit is provided that includes a surface-binding peptide or polypeptide disclosed herein. The peptide or polypeptide can bind, for example, a target atomic configuration, a flat surface, or another smooth surface, such as a smooth, curved surface. The kit, for example, can include at least two peptides or polypeptides that bind a flat surface or a smooth, curved surface. The peptides or polypeptides can be separate, or can be linked together. Furthermore, as disclosed above, the peptide or polypeptide can be associated with a nanocode. In certain aspects, the kit includes a population of nanocodes each linked to a surface-binding peptide or polypeptide disclosed herein.

In another aspect, the kit includes a phage display library and a flat, curved and/or smooth surface, or a surface with a target atomic configuration.

EXAMPLES

Example 1

Milenyi µMACS Platform Control: Phage Display Affinity Control for Miltenyi µMACS system A 5 mL liquid culture (in a 50 ml tube) of the *E. coli* in LB was prepared by picking a single colony from a Tet streak plate (less than 4 weeks old) and growing at 37° C. for about 4-6 hrs ($A_{600}$–0.5) with shaking (~250 rpm).

Three experiments were run in parallel as follows.

Experiment 1—µMACS Streptavidin Beads

Ten µL of 100 mM Tris pH 7.5 and 100 µL of MACS streptavidin beads were combined with 5 µL of phage (displaying random oligonucleotides), and the mixture was incubated for 5 minutes.

While waiting for phage to bind the beads, a µMACs column was prepared by placing the column in a magnetic holder and adding 100 µL of the µMACS equilibration buffer for oligonucleotide applications. The buffer was eluted (eluate is the column flow through), followed by the addition of 200 µL 10 mM Tris pH 7.5. The tris was eluted, and then a second aliquot of 200 µL 10 mM Tris was added. The tris was then eluted again.

The beads with phage were loaded onto the magnetic µMACS column. The supernatant was eluted.

The column (with the beads bound) was washed ten times with 200 µL of TBST (0.1% Tween20). Fractions five and ten were collected (denoted w5 and w10, respectively) and saved for analysis.

Bound phage were removed from the beads with 200 µL Glycine disruption buffer (0.2M glycine-HCl pH 2.2 with 1 mg/mL BSA). The reaction was immediately neutralized with 32 µL of 1 M Tris pH 9.0, and vortexed. This fraction was saved as D1. Disruption and neutralization steps were then repeated, and the fraction was saved as D2.

Experiment 2—µMACS Streptavidin Beads

Ten µL of 100 mM Tris pH 7.5 and 100 µL of µMACS streptavidin beads were combined with 5 µL of phage and incubated for 5 minutes.

While waiting for phage to bind, a µMACs column was prepared by placing the column in a magnetic holder, and adding 100 µL of the MACS equilibration buffer for oligonucleotide applications. The buffer was eluted (i.e., buffer was flown through the column), followed by the addition of 200 µL of 10 mM Tris pH 7.5 to the column. Tris was eluted, and then a second aliquot of 200 µL 10 mM Tris was added. Tris was eluted again.

The beads, containing bound phage, were loaded onto the column, and the flow through was eluted into sterile tube. Fifty µL of 10 mM Tris pH 7.5 was then added to the column, and eluted into the same tube. The column was then discarded.

One hundred µL of the µMACS beads, preincubated with capture target (Biotin —NNNNNNN, wherein N=A, T, C or G), were added to the flow through, and the reaction was carried out for 10 minutes.

While waiting for phage to bind, a second µMACs column was prepared by placing beads in magnetic holder and adding 100 µL of the MACS equilibration buffer for oligonucleotide applications. The buffer was eluted, followed by the addition of 200 µL 10 mM Tris pH 7.5. The Tris was eluted, and then a second aliquot of 200 µL 10 mM Tris was added. The Tris was eluted again.

The beads with phage (from para [0098]) were loaded onto the magnetic µMACS column. The flow through was eluted.

The beads (bound to column) were washed ten times with 200 µL of TBST (0.1% Tween20). Fractions five and ten were collected (labeled w5 and w10, respectively).

Bound phage were removed from the beads with 200 µL Glycine disruption buffer (0.2M glycine-HCl pH 2.2 with 1 mg/mL BSA). The reaction was immediately neutralized with 32 µL of 1 M Tris pH 9.0, followed by vortexing. This fraction was saved as D1. The reaction was then repeated with a second aliquot of disruption buffer, neutralized, and saved as D2.

Experiment 3—µMACS Streptavidin Beads

Ten µL of 100 mM Tris pH 7.5 and 100 µL of µMACS streptavidin beads were combined with 5 µL of phage, and incubated for 5 minutes.

While waiting for phage to bind, a µMACs column was prepared by placing the column in a magnetic holder, followed by adding 100 µL of the µMACS equilibration buffer for oligonucleotide applications to the column. The buffer was eluted, and then 200 µL of 10 mM Tris pH 7.5 was added to the column. The Tris was eluted, and then a second aliquot of 200 µL 10 mM Tris was added. The Tris was eluted again.

The beads, containing bound phage, were loaded onto the column, and the flow through was eluted into sterile tube. Fifty µL of 10 mM Tris pH 7.5 was then added to the column, and eluted into the same tube. The column was then discarded.

Ninety pmol of capture target (Biotin —NNNNNNN) was added to the phage into the same tube, and incubated for 15 minutes. Here N=A, T, C or G.

One hundred µL of the µMACS beads were added to the phage and target, and incubated for 10 minutes.

While waiting for phage to bind, a second µMACs column was prepared by placing the column in a magnetic holder and adding 100 µL of the MACS equilibration buffer for oligonucleotide applications. The buffer was eluted, followed by the addition of 200 µL of 10 mM Tris pH 7.5. The Tris was eluted, and then a second aliquot of 200 µL 10 mM Tris was added, followed by elution of the Tris.

The beads, target and phage (from para [0107]) were loaded onto the magnetic µMACS column. The flow through was eluted.

The column was washed ten times with 200 µL of TBST (0.1% Tween20). Fractions five and ten were collected (labeled w5 and w10, respectively).

Bound phage were removed from the column with 200 µL of Glycine disruption buffer (0.2M glycine-HCl pH 2.2 with 1 mg/ml BSA). The reaction was immediately neutralized with 32 μL of 1M Tris pH 9.0, vortexed, and saved as D1. The reaction was repeated with a second aliquot of glycine disruption buffer, neutralized, and saved as D2.

Washes 5, 10, D1 and D2 were titered for each experiment. Also, 1 μL of the stock phage was titered a positive control for the plating system.

The eluted phage was diluted at 100-fold (make two 90:10, LB:phage, serial dilutions) in LB and the 10 μL of the 100-fold diluted phage was added to 200 μL of *E. coli* liquid culture.

A pour plate was made by adding all of the diluted phage in LB with *E. coli* into 3 mL of melted top agar and immediately poured onto a warm LB+IPTG+Xgal plates. Plates were allowed to set for 10 minutes. Plates were kept inverted overnight in a 37° C. incubator.

The next day, the plates were removed and the blue plaques were counted. If desired, the plates can be sealed with parafilm, after removing, and stored at 4° C. in the dark. (The number of plaques per plate is equal to the number of phage/μL in the stock.)

Results were then tabulated and are shown below in Table 1.

TABLE 1

Results from control experiments

| Sample | Exp1-W5 | Exp1-W10 | Exp1-D1 | Exp1-D2 |
|---|---|---|---|---|
| Titer plaques/plate | ~600 | 57 | ~2100 | 213 |
| Titer plaques/plate | ~450 | 32 | ~840 | 89 |
| Titer plaques/plate | ~412 | 35 | ~400 | 187 |

Example 2

SERADYN (Carboxylated Microspheres) Platform Control

To attach an aminolated oligonucleotide (NH2-Q-Q-NNNNNNN) a five fold excess of EDC in 100 mM MES pH 6.0 was used. Here N equals A, T, C or G.

A 5 mL liquid culture (in a 50 ml tube) of the *E. coli* in LB was prepared by picking a single colony from a Tet streak plate (less than 4 weeks old) and growing at 37° C. for about 4-6 hrs ($A_{600}$ ~0.5) with shaking (~250 rpm).

The two experiments were run in parallel.

Experiment 1

One hundred μL of carboxylated beads were washed twice with 10 mM Tris pH 7.5.

Ninety five μL of Tris 10 mM pH 7.5 and 5 μL of phage were combined in a reaction tube and incubated for 10 minutes. The tube was placed in the magnet, and the supernatant was removed. The beads were washed ten times with 500 μL of TBST (0.1% Tween20). Fractions five and ten were collected (labeled w5 and w10, respectively).

Bound phage were removed with 200 μL of Z buffer TBST with 1 mM DTT and 1 μM degenerate oligo (disruption buffer), and saved as D1. This step was repeated and saved as D2.

Experiment 2

One hundred μL of Seradyn carboxylated beads were washed twice with 10 mM Tris pH 7.5.

Ninety five μL of Tris 10 mM pH 7.5 was combined with 5 μL of phage, and incubated for 10 minutes. Beads were isolated with magnet and supernatant was transferred to a second aliquot of 100 μL Serodyn beads (after washing second aliquot with Tris). The second aliquot of beads and had target oligonucleotide attached, and was washed with Tris prior to the supernatant transfer step. Once the supernatant was transferred, it was incubated for ten minutes with the beads.

The second aliquot of beads was washed ten times with 500 μL TBST (0.1% Tween20). Fractions five and ten were collected (labeled as w5 and w10, respectively).

Bound phage were removed from the beads with 200 μL Z buffer TBST with 1 mM DTT and 1 μM degenerate oligo (disruption step) and saved as D1. This step was repeated and saved as D2.

Titers

The eluted phage from the disruption step was diluted 100-fold (two 90:10, LB:phage, serial dilutions are made) in LB and then 10 μL of the 100-fold diluted phage was added to 200 μL of *E. coli* liquid culture. The phage from the wash steps were diluted by diluting 30 μL into 70 μL LB, followed by a ten to one dilution (10 μL of diluted phage and 90 μL LB). Ten μL of the second dilution was placed into 200 μL of *E. coli* liquid culture.

A pour plate was made by adding all of the diluted phage in LB with *E. coli* into 3 mL of melted top agar and immediately poured onto a warm LB+IPTG+Xgal plates. Plates were allowed to set for 10 minutes. Plates were kept inverted overnight in a 37° C. incubator.

The next day, the plates were removed and the blue plaques were counted. If desired, the plates can be sealed with parafilm, after removing, and stored at 4° C. in the dark. (The number of plaques per plate is equal to the number of phage/μL in the stock.)

Results were then tabulated, and are shown in Table 2.

TABLE 2

Results from control experiments

| Sample | Exp1-W5 | Exp1-W10 | Exp1-D1 | Exp1-D2 |
|---|---|---|---|---|
| Titer plaques/plate | 1250 | 72 | 576 | 53 |
| Sample | Exp2-W5 | Exp2-W10 | Exp2-D1 | Exp2-D2 |
| Titer plaques/plate | 1000 | 32 | 560 | 31 |

Example 3

Becton Dickenson's Streptavidin Coated Multi-Well Polystyrene Micro-Titer Plate: Phage Display Affinity Control-Polystyrene Plates This experiment was conducted to test for specific binding, nonspecific binding, wash efficiency and disruption efficiency.

The Streptavidin coated micro-titer plate is referred to throughout this example as the affinity platform (AP). APs were prepared by reconstituting in PBS for 15 minutes and attaching the appropriate targets.

A 5 mL liquid culture (in a 50 mL tube) of the *E. coli* in LB was prepared by picking a single colony from a Tet streak plate (less than 4 weeks old) and growing at 37° C. for about 4-6 hrs ($A_{600}$ –0.5) with shaking (~250 rpm).

Affinity platforms were set up as shown in Table 3.

TABLE 3

Summary of control reactions

| Reaction | target present? |
|---|---|
| Exp1AP-a | no |
| Exp2AP-a | no |
| Exp2AP-b | yes |
| Exp3AP-a | no |
| Exp3AP-b | no |

The target was a generic oligonucleotide labeled with biotin. (Biotin —NNNNNNN; N=A, T, C or G). The second plate (Exp 2AP-b) was preincubated with target prior to addition of the supernatant of Exp2AP-a.

Affinity platforms were washed with Tris buffer (10 mM pH 7.5).

Five µL of phage were placed into 150 µL of Tris buffer. One hundred fifty µL of diluted phage were added to Exp2AP-a and Exp3AP-a, and reacted for 30 minutes at 4° C. to allow for binding.

Next, the supernatant from Exp2AP-a was transferred to Exp2AP-b. The supernatant from Exp3AP-a was transferred to Exp3AP-b. Finally 150 µL of diluted phage was added to Exp1AP-a. All three reactions were conducted for 30 minutes at 4° C. with shaking.

Unbound phage were removed and plates were washed ten times with 175 µL of TBST (Tris 10 mM pH7.5, NaCl 150 mM and 0.1% Tween-20) for 5 minutes each at 4° C. with shaking. The wash solutions from the fifth and tenth washes were kept. The wash solutions were placed in reaction tubes and labeled as Exp1 W5, Exp2 W5, Exp3 W5, Exp1 W10, Exp2 W10 and Exp3 W10, respectively.

The bound phage were removed by adding 150 µL of glycine disruption buffer (0.2M glycine-HCl pH 2.2 with 1 mg/mL BSA) with 400 µg/mL BSA added fresh from a 20 mg/mL stock (i.e., add 3 µL of the BSA stock to the 150 µL of glycine buffer), and incubated for 9-10 minutes at 4° C. with shaking. Immediately, the reactions were neutralized with 25 µL of 1M Tris (pH 9.1). Tubes were labeled as Exp1-D1, Exp2-D1, Exp3-D1.

To remove any remaining phage from the APs, 150 µL of glycine disruption buffer (0.2M glycine-HCl pH 2.2 with 1 mg/mL BSA) with 400 µg/mL BSA added fresh from a 20 mg/mL stock was added to the APs, and incubated for 9-10 minutes at 4° C. with shaking, followed by immediate neutralization of the elution fraction with 25 µL of 1M Tris (pH 9.1). Tubes were labeled as Exp1-D2, Exp2-D2, Exp3-D2.

Results from first pan were titered as follows. The eluted phage were diluted at 100-fold (make two 90:10, LB:phage, serial dilutions) in LB and then 10 µL of the 100-fold diluted phage was added to 200 µL of *E. coli* liquid culture. The remaining undiluted phage were stored at 4° C.

A pour plate was made by adding all of the diluted phage in LB with *E. coli* into 3 mL of melted top agar and immediately poured onto a warm LB+IPTG+Xgal plates. Plates were allowed to set for 10 minutes. Plates were kept inverted overnight in a 37° C. incubator.

The next day, the plates were removed and the blue plaques were counted. If desired, the plates can be sealed with parafilm, after removing, and stored at 4° C. in the dark. (The number of plaques per plate is equal to the number of phage/µL in the stock.)

The titer results from these experiments are given in Table 4.

TABLE 4

Results from control experiments

| Sample | Exp1-W5 | Exp1-W10 | Exp1-D1 | Exp1-D2 |
|---|---|---|---|---|
| Titer plaques/plate | 1113 | 98 | 511 | 123 |
| Sample | Exp2-W5 | Exp2-W10 | Exp2-D1 | Exp2-D2 |
| Titer plaques/plate | 678 | 81 | 501 | 97 |
| Sample | Exp3-W5 | Exp3-W10 | Exp3-D1 | Exp3-D2 |
| Titer plaques/plate | 599 | 72 | 520 | 75 |

This example demonstrated that the Streptavidin coated plates can be used as APs and are compatible with all buffers are reagents. The similarities in the three experimental results were within one standard deviation, suggesting the plate has more nonspecific interactions with the original library than the other platforms. Thus, the plate is best used for downstream panning.

Example 4

Evolution Strategies for Peptides and Proteins that Bind Single Nucleotides

For each of these strategies, "pan" refers to the contacting step in the respective biopanning cycle.

Adenosine Binders

| Pan #1 | |
|---|---|
| Platform: | µMACS |
| Counter Selection: | Against µMACs system |
| Selection Target: | Biotin-NNNNNNN |
| Binding Buffer: | 10 mM Tris pH 7.6 |
| Wash Buffer: | TBST 0.1% |
| Disruption Buffer: | 10 mM DTT in TBST 0.1% with 10 uM $N_7$ |

| Pan #2 | |
|---|---|
| Platform: | µMACS |
| Counter Selection: | Against µMACs system with equal molar ratio of preloaded Biotin-$T_7$, Biotin-$C_7$ and Biotin-G7. |
| Selection Target: | Biotin-AAAAAAA |
| Binding Buffer: | 10 mM Tris pH 7.6 and 10 mM NaCl |
| Wash Buffer: | 1X TBST with 0.1% Tween 20, 10 mM NaCl, 1 µM of $T_7$, $G_7$ and $C_7$. |
| Disruption Buffer: | 10 mM Tris pH 7.5, 0.1% Tween 20, 1 mM NaCl, 100 uM AAAAAAA. |

| Pan #3 | |
|---|---|
| Platform: | Seradyn carboxylated magnetic microspheres |
| Counter Selection: | Against Seradyn beads with equal molar mixture of a single T, C and G. |
| Selection Target: | NH2-Sp18-A (single A) |
| Binding Buffer: | 10 mM Tris pH 7.6 and 10 mM NaCl |
| Wash Buffer: | 1X TBST with 0.1% Tween 20, 10 mM NaCl, 10 uM of T, G and C. |

Thymidine Binders

Pan #1

| | |
|---|---|
| Platform: | µMACS |
| Counter Selection: | Against uMACs system |
| Selection Target: | Biotin-NNNNNNN |
| Binding Buffer: | 10 mM Tris pH 7.6 |
| Wash Buffer: | TBST 0.1% |
| Disruption Buffer: | 10 mM DTT in TBST 0.1% with 10 µM $N_7$ |

Pan #2

| | |
|---|---|
| Platform: | µMACS |
| Counter Selection: | Against µMACs system with equal molar ratio of preloaded Biotin-$A_7$, Biotin-$C_7$ and Biotin-$G_7$. |
| Selection Target: | Biotin-TTTTTTT |
| Binding Buffer: | 10 mM Tris pH 7.6 and 10 mM NaCl |
| Wash Buffer: | 1X TBST with 0.1% Tween 20, 10 mM NaCl, 1 µM of $A_7$, $G_7$ and $C_7$. |
| Disruption Buffer: | 10 mM Tris pH 7.5, 0.1% Tween 20, 1 mM NaCl, 100 uM TTTTTTT. |

Pan #3

| | |
|---|---|
| Platform: | Seradyn carboxylated magnetic microspheres |
| Counter Selection: | Against Seradyn beads with equal molar mixture of a single A, C and G. |
| Selection Target: | NH2-Sp18-T (single T) |
| Binding Buffer: | 10 mM Tris pH 7.6 and 10 mM NaCl |
| Wash Buffer: | 1X TBST with 0.1% Tween 20, 10 mM NaCl, 10 uM of A, G and C. |
| Disruption Buffer: | 10 mM Tris pH 7.5, 0.1% Tween 20, 1 mM NaCl, 1 mM T. |

Cytosine Binders

Pan #1

| | |
|---|---|
| Platform: | µMACS |
| Counter Selection: | Against µMACs system |
| Selection Target: | Biotin-NNNNNNN |
| Binding Buffer: | 10 mM Tris pH 7.6 |
| Wash Buffer: | TBST 0.1% |
| Disruption Buffer: | 10 mM DTT in TBST 0.1% with 10 uM $N_7$ |

Pan #2

| | |
|---|---|
| Platform: | µMACS |
| Counter Selection: | Against µMACs system with equal molar ratio of preloaded Biotin-$A_7$, Biotin-$T_7$ and Biotin-$G_7$. |
| Selection Target: | Biotin-CCCCCCC |
| Binding Buffer: | 10 mM Tris pH 7.6 and 10 mM NaCl |
| Wash Buffer: | 1X TBST with 0.1% Tween 20, 10 mM NaCl, 1 µM of $A_7$, $G_7$ and $T_7$. |
| Disruption Buffer: | 10 mM Tris pH 7.5, 0.1% Tween 20, 1 mM NaCl, 100 µM CCCCCCC. |

Pan #3

| | |
|---|---|
| Platform: | Seradyn carboxylated magnetic microspheres |
| Counter Selection: | Against Seradyn beads with equal molar mixture of a single A, T and G. |
| Selection Target: | NH2-Sp18-T (single C) |
| Binding Buffer: | 10 mM Tris pH 7.6 and 10 mM NaCl |
| Wash Buffer: | 1X TBST with 0.1% Tween 20, 10mM NaCl, 10 uM of A, G and T. |
| Disruption Buffer: | 10 mM Tris pH 7.5, 0.1% Tween 20, 1 mM NaCl, 1 mM C. |

Guanine Binders

Pan #1

| | |
|---|---|
| Platform: | µMACS |
| Counter Selection: | Against µMACs system |
| Selection Target: | Biotin-NNNNNNN |
| Binding Buffer: | 10 mM Tris pH 7.6 |
| Wash Buffer: | TBST 0.1% |
| Disruption Buffer: | 10 mM DTT in TBST 0.1% with 10 uM $N_7$ |

Pan #2

| | |
|---|---|
| Platform: | µMACS |
| Counter Selection: | Against µMACs system with equal molar ratio of preloaded Biotin-$A_7$, Biotin-$T_7$ and Biotin-$C_7$. |
| Selection Target: | Biotin-GGGGGGG |
| Binder Buffer: | 10 mM Tris pH 7.6 and 10 mM NaCl |
| Wash Buffer: | 1X TBST with 0.1% Tween 20, 10 mM NaCl, 1 uM of $A_7$, $T_7$ and $C_7$. |
| Disruption Buffer: | 10 mM Tris pH 7.5, 0.1% Tween 20, 1 mM NaCl, 100 µM GGGGGGG. |

Pan #3

| | |
|---|---|
| Platform: | Seradyn carboxylated magnetic microspheres |
| Counter Selection: | Against Seradyn beads with equal molar mixture of a single A, T and C. |
| Selection Target: | NH2-Sp18-G (single G) |
| Binding Buffer: | 10 mM Tris pH 7.6 and 10 mM NaCl |
| Wash Buffer: | 1X TBST with 0.1% Tween 20, 10 mM NaCl, 10 uM of A, T and C. |
| Disruption Buffer: | 10 mM Tris pH 7.5, 0.1% Tween 20, 1 mM NaCl, 1 mM G. |

Example 5

Base Detector Evolution from a Cyclic Peptide Phage Display Library

On day 1, an *E. coli* host culture (ER2738) was started by streaking the glycerol stock of ER2738 onto a LB-Tet plate (Final concentration of Tet is 20 µg/mL). The plate was incubated overnight (inverted) and stored at 4° C. in the dark, sealed with parafilm. Individual colonies were then chosen to start liquid cultures for phage amplification and titers.

First Biopanning

A liquid culture of the E. coli was started by choosing a single colony from the Tet-plate (step IA) and inoculating 5 mL of LB. The culture was grown for about 4 hours to the appropriate density (~0.5 au $A_{600}$). This stock was to grow/titer the phage from the first pan.

First Pan—

Panning with NNNNNNN for ssDNA binders, wherein N is any nucleotide.

Ten µL of 100 mM Tris pH 7.5 was combined with 100 µL of µMACS streptavidin beads and 10 µL of phage, and incubated for 10 minutes.

While waiting for phage to bind, a µMACs column was prepared by placing the column in a magnetic holder and adding 100 µL (dropwise) of the µMACS equilibration buffer for oligonucleotide applications to the column. The equilibration buffer was eluted, and 200 µL of 10 mM Tris pH 7.5 was added, followed by elution. A second aliquot of 10 mM Tris was then added and eluted.

Beads with phage were loaded (dropwise) onto the column, and the flow through was eluted into a sterile tube. Fifty µL of 10 mM Tris pH 7.5 was added (dropwise) to the column, and eluted into the same tube. The column was then discarded.

Ninety pmol of capture target (Biotin-NNNNNNN) was added to the phage and incubated for 15 minutes (there should be thousands of probes available for each phage).

Next, 100 µL of the µMACs beads were added to the phage and incubated for 10 minutes. One hundred pmol of binding site is available in 100 µL of the beads, which should capture all biotin probes whether or not they are bound to phage.

While waiting for phage to bind, a second µMACs column was prepared by placing the column in a magnetic holder and adding 100 µL of the µMACs equilibration buffer for oligonucleotide applications to the column. The buffer was then eluted, followed by addition of 200 µL 10 mM Tris pH 7.5. Tris was eluted, a second aliquot of 10 mM Tris was added and eluted. The beads with phage were loaded onto the magnetic MACs column (dropwise), and the flow through was eluted.

The column was washed ten times with 500 µL of TBST (0.1% Tween20). The first two washes were added (dropwise). Fractions five and ten were collected as controls (labeled as w5 and w10, respectively).

Two hundred µL of DTT solution (i.e., Z buffer 1 mM DTT) was combined with 10 µM of the NNNNNN-Biotin probe to create a disruption ("bump") buffer. Twenty µL of the bump buffer was added to the column every minute for ten consecutive minutes and the flow through was eluted into a sterile tube.

Titer Results from First Pan

Results from first pan were titered as follows. The eluted phage were diluted at 100-fold (make two 90:10, LB:phage, serial dilutions) in LB and then 10 µL of the 100-fold diluted phage was added to 200 µL of E. coli liquid culture. The remaining undiluted phage were stored at 4° C.

A pour plate was made by adding all of the diluted phage in LB with E. coli into 3 mL of melted top agar and immediately poured onto a warm LB+IPTG+Xgal plates. Plates were allowed to set for 10 minutes. Plates were kept inverted overnight in a 37° C. incubator.

The next day, the plates were removed and the blue plaques were counted. If desired, the plates can be sealed with parafilm, after removing, and stored at 4° C. in the dark. (The number of plaques per plate is equal to the number of phage/µL in the stock.)

Wash 10 had 72 colonies. Bump had 271 colonies. The results indicated the process was successful, and that all components worked as expected.

Phage Amplification of "Winners" from Pan #1

A liquid culture was started (~3-5 mL) of ER2738 by choosing a single colony from the original Tet streak plate and inoculating LB broth with 20 µg/mL Tetracycline (added from a 20 mg/mL stock). The culture was incubated overnight at 37° C. with shaking.

At day 3, the liquid culture was removed from the incubator. Five (labeled A, T, C, G and Strept, respectively) 20 mL cultures were prepared by adding 20-30 mL of LB to a sterile 250 mL flask with 200 µL of the ER2738 liquid culture (100 fold dilution). The remaining eluted phage from one of the first pannings was added to one of the flasks and labeled accordingly, and repeated for all five samples (A, T, C, G and Strept). The phage/E coli mixture was incubated for 4-5 hours at 37° C. with shaking.

Phage Purification

The phage/E. coli cultures were removed from the incubator and transferred to clean, sterile, labeled Oak Ridge tubes, followed by centrifugation at 10,000 rpm for 15 minutes to pellet the E. coli (pellet was firm and visible—approximately 1 cm×1 cm). The solution containing phage was transferred (e.g., by decanting) to another Oak Ridge tube and re-centrifuged to assure all E. coli were removed. The supernatant was removed by decanting, being careful not to carry any E. coli over when transferring. It is preferred to leave some culture behind rather than chance contaminating the phage with carried-over E. coli. Once again, the phage were transferred to a clean Oak Ridge tube.

Phage were precipitated by adding about 3.3-5 mL of sterile 20% PEG (8000) and 2.5 M NaCl to the 20 µL phage to give a final concentration of PEG at 3%. The phage were placed at 4° C. for more than one hour, preferably overnight (~20 hours).

At day 4, phage were recovered as follows. A 3 mL liquid culture of E. coli was started for tittering recovered phage. Precipitated phage were removed from 4° C. and centrifuged in an Oak Ridge tube at 12,000 rpm for 20 minutes. The supernatant was decanted and phage pellet was kept. The tube was inverted to allow the remaining liquid to drain onto absorbent disposable towels. There was a white pellet of phage about 5 mm in diameter.

The pellet was resuspended in 1 mL TBS by repetitive pipetting. The 1 mL solution was then transferred to a 2 mL reaction tube and centrifuged at max speed for 10 minutes to pellet any E. coli or unwanted debris. The supernatant was transferred to a clean reaction tube. One hundred seventy µL of the 20% PEG 8000, 2.5M NaCl was added to each sample (A, T, C, G and Strept) to re-precipitate the phage.

The sample tubes were placed at 4° C. for at least 1 hour (overnight—19 hours is OK). The tubes were centrifuged at 4° C. on the highest speed setting for 10 minutes to pellet the phage. The supernatants were removed and the respective pellets were kept. The pellets (purified phage from first biopanning) were each resuspended in 200 µL of TBS containing 0.02% azide. The resuspension took several minutes with vigorous pipetting and tube flicking.

The purified phage was then titered as follows. A 3 mL liquid culture of E. coli in LB was prepared and grown for 4 hours. For each target (A, T, C, G and Strept), a set of serial dilutions was prepared (11 in total including starting stock, 90 µL TBS: 10 µL phage stock or dilution).

The $9^{th}$, $10^{th}$ and $11^{th}$ dilutions were plated. The remaining undiluted phages were stored at 4° C. Ten µL of the diluted phage was added to 200 µL of E. coli liquid culture, and incubated for 10 minutes. A pour plate was then made by adding all of the phage infected E. coli to 3 mL of melted top agar. This mixture was immediately poured on warm LB+IPTG+Xgal plates, and kept in a 37° C. incubator overnight. The following day, the plates were removed and the blue plaques were counted. The plates were then resealed with parafilm and stored at 4° C. in the dark. If more than 200 plaques or less than 5 plaques were formed on a single plate, the cultures were re-titered and plated to give ~10-200 plaques per plate prior to picking colonies for sequencing. Titer results follow:

Dilution #9, 21 plaques; Dilution #10, 3 plaques; Dilution #11, no plaques. Phage amplification resulted in $0.5 \times 10^{13}$ PFU/mL.

Second Round of Biopanning—Counterselection

Poly A, T, C or G. In the following pan, four experiments were executed using the same starting phage winners (i.e., blue phage plaques) from the first pan. At this point, the binders of specific nucleotides were separated from the binders of random nucleotides. Three of the four homo-oligomers were used for counter selection against the respective target. For example, when selecting for A binders, poly T, C and G were added to the respective phage from the first pan.

Four stocks of beads were prepared—one for A, T, C and G. The following reactions took place at standard temperature and pressure (STP) for 15 minutes.

One hundred µL µMACS were combined with 4 µL of a 20 pmol/µL stock of Biotin-AAAAAAA (A1), Biotin-TTTTTTT (A2), Biotin-CCCCCCC (A3) or Biotin-GGGGGGG (A4) in separate reaction tubes.

Four counter selection reactions were prepared as follows. Thirty µL of A2, A3 and A4 and 20 µL of phage from first pan, and 10 µL 100 mM Tris buffer were combined and reacted for 15 minutes. This reaction was called reaction A.

Thirty µL of A1, A3 and A4 and 20 µL of phage from first pan, and 10 µL 100 mM Tris buffer were combined and reacted for 15 minutes. This reaction was called reaction B.

Thirty µL of A1, A2 and A4 and 20 µL of phage from first pan, and 10 µL 100 mM Tris buffer were combined and reacted for 15 minutes. This reaction was called reaction C.

Thirty µL of A1, A2 and A3 and 20 µL of phage from first pan, and 10 µL 100 mM Tris buffer were combined and reacted for 15 minutes. This reaction was called reaction D.

Four µMACS columns were then prepared by pre-wetting column with 100 µL of the DNA application buffer followed by three 200 µL column washes with 10 mM Tris buffer.

Each reaction A, B, C and D was loaded dropwise onto its own column, and the flow through was collected in a sterile tube. Fifty µL 10 mM Tris, 10 mM NaCl buffer was added to the column and the flow through collected in the same sterile tube. This was the pan2 counter selection phage stock.

Positive Selection

Four positive selection reactions were set up as follows:

Reaction A. The flow through from counter selection reaction A (about 150 µL) was combined with 90 pmol of Biotin-AAAAAAA (4.5 µL from a 20 pmol/µL stock), 3 µL of 100 mM NaCl and reacted for 30 minutes. Next, 100 µL of the MACS beads was added to the mixture and reacted for 15 minutes under standard temperature and pressure (STP).

Reaction B. The flow through from counter selection reaction B (about 150 µL) was combined with 90 pmol of Biotin-TTTTTTT (4.5 µL from a 20 pmol/µL stock), 3 µL of 100 mM NaCl and reacted for 30 minutes. Next, 100 µL of the MACS beads was added to the mixture and reacted for 15 minutes under STP.

Reaction C. The flow through from counter selection reaction C (about 150 µL) was combined with 90 pmol of Biotin-CCCCCCC (4.5 µL from a 20 pmol/µL stock), 3 µL of 100 mM NaCl and reacted for 30 minutes. Next, 100 µL of the MACS beads was added to the mixture and reacted for 15 minutes under STP.

Reaction D. The flow through from counter selection reaction C (about 150 µL) was combined with 90 pmol of Biotin-GGGGGGG (4.5 µL from a 20 pmol/µL stock), 3 µL of 100 mM NaCl and reacted for 30 minutes. Next, 100 µL of the MACS beads was added to the mixture and reacted for 15 minutes under STP.

While incubating the four reactions A, B, C and D, four MACS columns were pre-wet with the DNA application buffer. The columns were then washed three times with 200 µL of 10 mM Tris.

Each reaction was loaded dropwise onto its own column. Next, the columns were washed 20 times with 200 µL of the following buffers. The $20^{th}$ wash was collected for titer analysis.

Reaction A wash buffer—1×TBST with 0.1% Tween 20, 10 mM NaCl, µM of $T_7$, $G_7$ and $C_7$.

Reaction B wash buffer—1×TBST with 0.1% Tween 20, 10 mM NaCl, µM of $A_7$, $G_7$ and $C_7$.

Reaction C wash buffer—1×TBST with 0.1% Tween 20, 10 mM NaCl, µM of $A_7$, $T_7$ and $G_7$.

Reaction D wash buffer—1×TBST with 0.1% Tween 20, 10 mM NaCl, µM of $A_7$, $T_7$ and $C_7$.

Bound phage were removed from each column with 200 µL of the following bump ("disruption") buffers (50 µL every 2 minutes for a total of four 50 µL elutions). The eluted phage (in the flow through portion) were collected.

Reaction A bump buffer—10 mM Tris pH 7.5, 0.1% Tween 20, 1 mM NaCl, 100 uM AAAAAAA.

Reaction B bump buffer—10 mM Tris pH 7.5, 0.1% Tween 20, 1 mM NaCl, 100 uM TTTTTT.

Reaction C bump buffer—10 mM Tris pH 7.5, 0.1% Tween 20, 1 mM NaCl, 100 uM CCCCCCC.

Reaction D bump buffer—10 mM Tris pH 7.5, 0.1% Tween 20.1 mM NaCl, 100 uM GGGGGGG.

Phage were then titered from the second round of panning.

Eluted phage were diluted 100-fold (make two 90:10, LB:phage, serial dilutions) in LB and then 20 µL of the 100-fold diluted phage was added to 200 µL of E. coli liquid culture. The remaining undiluted phage were stored at 4° C. A pour plate was made by adding all of the diluted phage in LB to 3 mL of melted top agar, followed by immediately pouring this mixture on warm LB+IPTG+Xgal plates. Plates were kept in 37° C. incubator overnight.

The next day, plates were removed and the blue plaques were counted. The plates were resealed with parafilm and stored at 4° C. in the dark. The results are given in Table 5.

TABLE 5

| Titer results from $2^{nd}$ round of panning | |
|---|---|
| Name | Titer |
| Reaction A Wash | 1 |
| Reaction B Wash | 25 |
| Reaction C Wash | 15 |
| Reaction D Wash | 14 |
| Reaction A bump | 159 |
| Reaction B bump | 124 |
| Reaction C bump | 210 |
| Reaction D bump | 190 |

Phage Amplification of "Winners" from Pan #2

A liquid culture was started (~3-5 mL) of ER2738 by choosing a single colony ("winners") from the original Tet streak plate and inoculating LB broth with 20 µg/mL Tetracycline (added from a 20 mg/mL stock). The culture was incubated overnight at 37° C. with shaking.

At day 3, the liquid culture was removed from the incubator. Five (A, B, C and D and control) 20 mL cultures were prepared by adding 20-30 mL of LB to a sterile 250 mL flask with 200 µL of the ER2738 liquid culture (100 fold dilution). Again, A, B, C and D correspond to selection for the nucleotides A, T, C and G, respectively. The remaining eluted phage from one of the respective second pannings were added to one of the flasks and labeled accordingly, and repeated for all five samples (A, B, C and D and control). The phage/*E coli* mixture was incubated for 4-5 hours at 37° C. with shaking.

Phage Purification

Phage were purified as described above in this example, for the first round of biopanning, with one exception. Here, the $8^{th}$ dilution was plated as well. The results are shown in Table 6.

TABLE 6

| Name | Plaques on plate for dilution 8 | PFU/ mL |
|---|---|---|
| A selection - amplified | 440 | $4.4 \times 10^{12}$ |
| T selection - amplified | 101 | $1.0 \times 10^{12}$ |
| C selection - amplified | 105 | $1.0 \times 10^{12}$ |
| G selection - amplified | 32 | $1.3 \times 10^{12}$ |

Third Round of Panning—Counterselection

In this pan, four experiments were executed using the respective phage winners from the second pan. At this point, the specific distinct nucleotide binders (single base binders) were separated from the pool of N binders using negative counter-selection with individual nucleotides and positive selection for $A_7$, $T_7$, $C_7$, and $G_7$ oligonucleotides. In this round, competitive wash and disruption (bump) buffers having of single nucleotide bases were used.

Four stocks of beads were prepared—one for A, T, C and G—using aminolated monomer probes (5'NH3-[C3]-Spacer 18-N, wherein N=A, T, C or G). The reactions were set up as described for condensation of amide with a carboxyl group using carbodiimide catalyst. These reactions could have been set up one week in advance, if desired.

Two hundred µL of Serodyn beads (solvent removed and beads washed 3 times), for each reaction, were combined with 100 µg EDC and either 10 nmol of aminolated A, T, C or G probe in 200 µL of 100 mM MES.

Four counter selections were set up as follows:

Thirty µL of T, C and G beads and 20 µL of phage from second pan "A selection" were combined with 10 µL 100 mM Tris buffer, and reacted for 15 minutes. This was called Reaction A.

Thirty µL of A, C and G beads and 20 µL of phage from second pan "T selection" were combined with 10 µL 10 mM Tris buffer, and reacted for 15 minutes. This was called Reaction T.

Thirty µL of A, T and G beads and 20 µL of phage from second pan "C selection" were combined with 10 µL 100 mM Tris buffer and reacted for 15 minutes. This was called Reaction C.

Thirty µL of A, T and C beads and 20 µL of phage from second pan "G selection" were combined with 10 µL 100 mM Tris buffer and reacted for 15 minutes. This was called Reaction G.

While the counter selection proceeded, four tubes (labeled A, T, C and G, respectively) were prepared with 100 µL of the appropriate labeled beads (i.e., A, T, C or G), and a magnet was used to separate the beads from the supernatant. The supernatant was then removed and the beads were washed twice with 100 µL TE buffer.

A magnet was used to capture the beads from counter selection reaction, and the supernatant was transferred from the reaction tube to a clean tube. Next, the counter selection reaction A supernatant solution was transferred onto A beads (from para [0229]), and incubated together.

After incubation with the respective supernatant, the A, T, C and G beads were washed twenty times with 200 µL of the following buffers, depending on the reaction. The $20^{th}$ wash was collected for titer analysis.

Reaction A wash buffer—1×TBST with 0.1% Tween 20, 10 mM T, C and G.

Reaction T wash buffer—1×TBST with 0.1% Tween 20, 10 mM of A, C and G.

Reaction C wash buffer—1×TBST with 0.1% Tween 20, 10 mM of A, T, and G.

Reaction G wash buffer—1×TBST with 0.1% Tween 20, 10 uM of A, T and C.

Bound phage were removed with the 200 µL of the following buffer (incubated for 15 minutes). The magnet was used to isolate beads and collect eluted phage (in the supernatant).

Reaction A bump buffer—Z buffer, 1 mM A; Reaction T bump buffer—Z buffer, 1 mM T; Reaction C bump buffer—Z buffer, 1 mM C; and Reaction G bump buffer—Z buffer, 1 mM G.

Third Round of Panning—Titer Results.

Eluted phage were diluted 100-fold (make two 90:10, LB:phage, serial dilutions) in LB and then 20 µL of the 100-fold diluted phage was added to 200 µL of *E. coli* liquid culture. The remaining undiluted phage were stored at 4° C. A pour plate was made by adding all of the diluted phage in LB to 3 mL of melted top agar, followed by immediately pouring this mixture on warm LB+IPTG+Xgal plates. Plates were kept in a 37° C. incubator overnight.

The next day, plates were removed and the blue plaques were counted. The plates were sealed with parafilm and stored at 4° C. in the dark. The results are given in Table 7.

TABLE 7

| Titer results from $3^{rd}$ round of panning | |
|---|---|
| Name | Titer |
| Reaction A Wash | 220 |
| Reaction T Wash | 110 |
| Reaction C Wash | 122 |
| Reaction G Wash | 210 |
| Reaction A bump | 1016 |
| Reaction T bump | 520 |
| Reaction C bump | 524 |
| Reaction G bump | 832 |

Phage Amplification and Purification of the "Winners" from the $3^{rd}$ Round of Panning Phage were amplified as described from the winners of the second round of panning. The Results follow in Table 8.

TABLE 8

| Name | Plaques on plate for dilution 9 | PFU/mL |
|---|---|---|
| A selection - amplified | 31 | $3.1 \times 10^{12}$ |
| T selection - amplified | 46 | $4.6 \times 10^{12}$ |
| C selection - amplified | 52 | $5.2 \times 10^{12}$ |
| G selection - amplified | 99 | $9.9 \times 10^{12}$ |

Example 6

Analysis of Evolved Libraries

A liquid culture of K12 *E. coli* was started in 5 mL of LB by picking a single colony from a tetracycline plate (plate no older than 4 weeks).

Reaction Set Up

Streptavidin-coated micro titer plates were pre-incubated with 120 µL of PBS at room temperature for 15 minutes with shaking (240 rpm). Plates were washed two times with 120 µL of PBS and once with PBS/NaHC0$_3$.

The columns and rows of the micro titer plates were set up as follows. Column 1 tested library A, Column 2 tested library T, Column 3 tested library C, Column 4 tested library G, Column 5 tested the original library. Row one used A as a target, row 2 used T as a target, row 3 used C as a target, row 4 used G target and row five had no target (as a non-specific platform control).

The appropriate target (420 pmol) in 120 µL of PBS with 10 mM NaHC0$_3$ pH 7.4 was added to each row. Row 1 received Biotin Sp18 A, row 2 received Biotin Sp18 T, row 3 received Biotin Sp18 C and row 4 received Biotin Sp18 G. Row five was without target. Reactions were incubated for 15 minutes at room temperature with shaking (200 rpm), followed by five washes with 120 µL PBS/NaHC0$_3$.

The phage from the appropriate library (10 µL of phage and 110 µL of PBS/NaHC0$_3$) were added to the appropriate wells. Column A received the pan 3 of the A library, Column B received the pan 3 of the T library, Column C received the pan 3 of the C library, Column D received the pan 3 of the G library, Column E received the original library. All titers were adjusted to $10^{13}$ pfu/mL before adding. The reactions incubated for 15 minutes.

The wells were then washed once with 120 µL of PBS/NaHC0$_3$.

Next, the wells were washed five times with 130 µL TBST 0.1%, 5 times with 140 µL TBST 0.1%, five times with 145 µL TBST 0.1% and 15 times with 150 µL TBST 0.1%, for a total of 30 washes. The last wash was kept for titer analysis.

Row 1 was then bumped (disrupted) with 150 µL of 5 mM A in TBST. Row 2 was bumped with 150 µL of 5 mM T in TBST. Row 3 was bumped with 150 µL of 5 mM C in TBST. Row 4 was bumped with 150 µL of 5 mM G in TBST. Row 5 was bumped with 150 µL of 5 mM N in TBST. Each of these bump reactions took place for fifteen minutes at standard temperature and pressure. Bumps were kept for titer analysis.

Rows were bumped a second time with 150 µL of 10 mM DTT for 15 minutes at STP and kept for titer analysis.

The following were titered: the last wash (i.e, #30 bump), the bump (with nucleotide) and DTT bump at 200:1 dilution, for each titer (use 5 µL dilutant with 95 µL *E. coli* and 1 mL of top melt). These results are also shown graphically in FIGS. 1-3, respectively.

TABLE 9

Titer of wash #30

| | Library | | | | |
|---|---|---|---|---|---|
| Target | A | T | C | G | X |
| B-Sp18-A | 2 | 1 | 2 | 5 | 12 |
| B-Sp18-T | 1 | 3 | 1 | 4 | 5 |
| B-Sp18-C | 1 | 3 | 4 | 2 | 4 |
| B-Sp18-G | 0 | 4 | 2 | 4 | 7 |
| None | 2 | 3 | 4 | 7 | 10 |

TABLE 10

Titer of Bump with specific nucleotide

| | Library | | | | | | |
|---|---|---|---|---|---|---|---|
| Target | A | T | C | G | X | | |
| B-Sp18-A | 27 | 2 | 3 | 5 | 12 | 5 mM A | Bump |
| B-Sp18-T | 1 | 21 | 1 | 3 | 7 | 5 mM T | |
| B-Sp18-C | 2 | 3 | 18 | 4 | 4 | 5 mM C | |
| B-Sp18-G | 2 | 4 | 1 | 34 | 5 | 5 mM G | |
| None | 4 | 3 | 5 | 7 | 6 | 5 mM N | |

TABLE 11

Titer of non-specific DTT wash

| | Library | | | | |
|---|---|---|---|---|---|
| Target | A | T | C | G | X |
| B-Sp18-A | 15 | 1 | 2 | 3 | 10 |
| B-Sp18-T | 1 | 10 | 3 | 3 | 14 |
| B-Sp18-C | 3 | 4 | 18 | 9 | 17 |
| B-Sp18-G | 6 | 10 | 7 | 54 | 9 |
| None | 16 | 14 | 8 | 30 | 12 |

DISCUSSION

Table 9 shows that the 30 washes gave low numbers for all libraries and targets. In general, the original library (X) showed slightly higher numbers, as expected, due to nonspecific binders to the platform.

Table 10 shows the titer after specific bump with 5 mM nucleotide. This concentration of nucleotide in the wash buffer does not change the total ionic strength or pH. Most significantly, the results indicate the evolved libraries have an average of ten fold specificity preference for their respective base. By comparing Tables 9 and 10, a significant jump in titer only for the corresponding match of bump and target was seen. The low numbers for non-matching target and bump indicate the bump was affecting phage bound to target and not the platform itself. The original library also showed little affect from the 5 mM nucleotide. Thus, the addition of competitive nucleotide indicated the evolved libraries have gained a ten fold specificity for their respective base when compared to the other libraries or targets.

Tables 10 and 11 are similar in the trend each exhibits. These results show the libraries have also gained a increased affinity. The DTT should have disrupted all binding, and only the matching library to target gave an increased titer.

Example 7

Sequences Identified by Evolution Experiments

Each library was serially diluted and plated with *E. coli* on IPTG-Xgal plates to obtain isolated phage clones. Dilution factors of $10^8$ to $10^{10}$ were required to obtain isolated clones. Ten to twenty clones from each library were picked and cultured in 1.5 mL cultures of the appropriate *E. coli* host strain (ER 2738) for a period of 4 hours at 37° C. Cultures were transferred to 1.5 mL microfuge tubes and centrifuged twice at 15,000 rpm for 10 minutes to remove cells. A small volume of each culture supernatant containing phage was then diluted 100 fold and subjected to automated DNA cycle sequencing.

For unambiguous sequencing it was preferable to use multiple primers in independent sequencing reactions to obtain multiple independent reads of the target region. Accurate sequences were obtained for six clones each from the C and G libraries as shown below. Among this small number of independent clones, two clones (from the C library) showed exact consensus at all base positions, while others showed more general consensus among various positions. Unique sequences are given in Table 12.

TABLE 12

Sequences identified by Phage Display

| A library | T library | C library | G library |
|---|---|---|---|
| CHLHLSRSC (SEQ ID NO: 1) | CAPPSGTTC (SEQ ID NO: 8) | CNHEPRATC (SEQ ID NO: 14) | CRIPQIRDC (SEQ ID NO: 22) |
| CLPQNNRDC (SEQ ID NO: 2) | CDVTHIRHC (SEQ ID NO: 9) | CGHLKTEKC (SEQ ID NO: 15) | CRTGETAPC (SEQ ID NO: 23) |
| CPLKWWWPC (SEQ ID NO: 3) | CLQPDKYAC (SEQ ID NO: 10) | CGPRWAAPC (SEQ ID NO: 16) | CESSYTRAC (SEQ ID NO: 24) |
| CPPLRNPGC (SEQ ID NO: 4) | CPSRLLHPC (SEQ ID NO: 11) | CIRTQPSTC (SEQ ID NO: 17) | CHWLNVYQC (SEQ ID NO: 25) |
| CPYQKLPHC (SEQ ID NO: 5) | CSPKQFPNC (SEQ ID NO: 12) | CIFHS SQRC (SEQ ID NO: 18) | CIPTLTTAC (SEQ ID NO: 26) |
| CTHSLTIQC (SEQ ID NO: 6) | CTTKLGQAC (SEQ ID NO: 13) | CLPLPRTHC (SEQ ID NO: 19) | CLVSLAS SC (SEQ ID NO: 27) |
| CYHVAHQHC (SEQ ID NO: 7) | | CSTKAWNWC (SEQ ID NO: 20) | CKAASIDRC (SEQ ID NO: 28) |
| | | CTLSAPYTC (SEQ ID NO: 21) | CKVQSSLRC (SEQ ID NO: 29) |
| | | | CLHGPS STC (SEQ ID NO: 30) |
| | | | CFALQAWNC (SEQ ID NO: 31) |
| | | | CSSMAPKNC (SEQ ID NO: 32) |
| | | | CTRTTPALC (SEQ ID NO: 33) |
| | | | CTKFRLPQC (SEQ ID NO: 34) |

Although the invention has been described above, it will be understood that modifications and variations are encompassed within the spirit and scope of the invention. Accordingly, the invention is limited only by the following claims.

The invention claimed is:

1. A method for identifying a peptide comprising:
   incubating a first peptide library with a first set of nucleic acid oligonucleotides to identify a first sub-library of peptides that bind the first set of nucleic acid oligonucleotides;
   separating the first sub-library from the first library;
   contacting the first sub-library with a second set of nucleic acid oligonucleotides comprising homo-oligomers of nucleotides other than a preselected nucleotide, to identify a second sub-library of peptides that do not bind the second set of nucleic acid oligonucleotides;
   separating the second sub-library from the first sub-library;
   contacting the second sub-library with a third subset of nucleic acid oligonucleotides comprising a homogeneous population of homo-oligonucleotides comprising the pre-selected nucleotide and no other nucleotides, to identify a third sub-library of peptides that bind to the third subset of nucleic acid oligonucleotides;
   separating the third sub-library from the second sub-library;
   contacting the third sub-library with a plurality of a first set of aminolated nucleotides comprising a heterogeneous population of nucleotides other than the pre-selected nucleotide, to identify a fourth sub-library of peptides that do not bind the first set of aminolated nucleotides;
   separating the fourth sub-library from the fifth sub-library; and
   contacting the fifth sub-library with a second set of aminolated nucleotides, comprising a homogeneous population of the pre-selected nucleotide, to produce a sixth sub-library of peptides that bind the second set of aminolated nucleotides, thereby identifying a peptide that binds the pre-selected nucleotide.

2. "The method of claim 1, wherein at least one of the separations is carried out with a solid phase."

3. "The method of claim 2, wherein the solid phase comprises magnetic particles."

4. "The method of claim 1, wherein the first peptide library comprises a cyclic peptide phage display library."

5. "The method of claim 1, wherein the pre-selected nucleotide comprises a non-natural or a natural nucleotide."

6. "The method of claim 1, wherein the homo-oligonucleotides comprise five to ten nucleotides."

* * * * *